(12) United States Patent
Lalwani et al.

(10) Patent No.: US 10,821,276 B2
(45) Date of Patent: Nov. 3, 2020

(54) SYSTEM AND METHOD TO LOCALLY DELIVER THERAPEUTIC AGENT TO INNER EAR

(71) Applicant: The Trustees of Columbia University in the City of New York, New York, NY (US)

(72) Inventors: Anil K. Lalwani, New York, NY (US); Jeffrey W. Kysar, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 505 days.

(21) Appl. No.: 14/667,322

(22) Filed: Mar. 24, 2015

(65) Prior Publication Data
US 2015/0265824 A1    Sep. 24, 2015

Related U.S. Application Data

(63) Continuation-in-part of application No. PCT/US2013/075105, filed on Dec. 13, 2013.
(Continued)

(51) Int. Cl.
*A61M 5/00*    (2006.01)
*A61M 37/00*   (2006.01)

(52) U.S. Cl.
CPC ... *A61M 37/0015* (2013.01); *A61M 2037/003* (2013.01); *A61M 2037/0023* (2013.01);
(Continued)

(58) Field of Classification Search
CPC ...... A61M 37/0015; A61M 2037/0061; A61M 2037/003; A61M 2037/0023;
(Continued)

(56) References Cited

U.S. PATENT DOCUMENTS

| | | | | |
|---|---|---|---|---|
| 6,045,528 A | * | 4/2000 | Arenberg | A61F 11/002 604/28 |
| 6,377,849 B1 | * | 4/2002 | Lenarz | A61F 11/00 604/174 |

(Continued)

FOREIGN PATENT DOCUMENTS

EP          0989868         4/2000

OTHER PUBLICATIONS

Nguyen, Y et al. Cochlear Implant Insertion Forces in Microdissected Humao Cochlea to Evaluate a Prototype Array. Audiology and Neurotology. May 30, 2012; vol. 17, p. 297, col. 2, lines 17-21.
(Continued)

*Primary Examiner* — Rebecca E Eisenberg
(74) *Attorney, Agent, or Firm* — Reed Smith LLP; Lisa A. Chiarini

(57) ABSTRACT

The disclosed subject matter relates to a system and method for delivery of therapeutic agent to the inner ear. The system includes a plurality of micro-needles which can be delivered to the round window membrane by a delivery device, e.g. catheter, and is capable of controlled penetration of the round window membrane to create temporary and self-closing perforations. In some embodiments the micro-needles are hollow with a lumen for local drug delivery into the perforations. In other embodiments the micro-needles are solid and include a coating of therapeutic agent on exterior surface for delivery into the perforations.

20 Claims, 32 Drawing Sheets

Related U.S. Application Data

(60) Provisional application No. 61/969,714, filed on Mar. 24, 2014, provisional application No. 61/981,458, filed on Apr. 18, 2014, provisional application No. 61/833,849, filed on Jun. 11, 2013, provisional application No. 61/737,285, filed on Dec. 14, 2012.

(52) U.S. Cl.
CPC ............... *A61M 2037/0046* (2013.01); *A61M 2037/0053* (2013.01); *A61M 2037/0061* (2013.01)

(58) Field of Classification Search
CPC .. A61M 2037/0046; A61M 2210/0662; A61M 2210/0668; A61M 2210/0675
See application file for complete search history.

(56) References Cited

U.S. PATENT DOCUMENTS

| | | | |
|---|---|---|---|
| 6,611,707 B1* | 8/2003 | Prausnitz | A61B 5/14514 604/21 |
| 6,685,697 B1 | 2/2004 | Arenberg et al. | |
| 8,257,324 B2 | 9/2012 | Prausnitz et al. | |
| 2002/0133129 A1* | 9/2002 | Arias | A61M 37/0015 604/272 |
| 2003/0208167 A1* | 11/2003 | Prausnitz | A61B 5/14514 604/272 |
| 2005/0209565 A1 | 9/2005 | Yuzhakov et al. | |
| 2006/0195067 A1* | 8/2006 | Wolter | A61K 9/0021 604/265 |
| 2006/0264897 A1 | 11/2006 | Lobl et al. | |
| 2007/0038181 A1* | 2/2007 | Melamud | A61B 17/3478 604/158 |
| 2007/0078376 A1 | 4/2007 | Smith | |
| 2007/0018543 A1 | 8/2007 | Etheredge, III et al. | |
| 2008/0065002 A1 | 3/2008 | Lobl et al. | |
| 2011/0224629 A1 | 9/2011 | Jolly et al. | |
| 2011/0030685 A1 | 12/2011 | Black et al. | |
| 2011/0301681 A1 | 12/2011 | Risi | |
| 2012/0021416 A1 | 1/2012 | Zassenhaus | |
| 2012/0245419 A1 | 9/2012 | Makower et al. | |
| 2015/0080802 A1* | 3/2015 | Kang | A61M 37/0015 604/173 |

OTHER PUBLICATIONS

Geerligs, M et al. In Vitro Indentation to Determine the Mechanical Properties of Epidermis. Journal of Biomechanics. Apr. 7, 2011; vol. 44, No. 6, p. 1178, col. 1, lines 16-25.
Extended European Search Report dated Jun. 13, 2016 in Application No. 13862239.4.
International Search Report dated Feb. 24, 2014 in Application No. PCT/US2013/075105.
International Preliminary Report on Patentability dated Jun. 16, 2015 in Application No. PCT/US2013/075105.

* cited by examiner

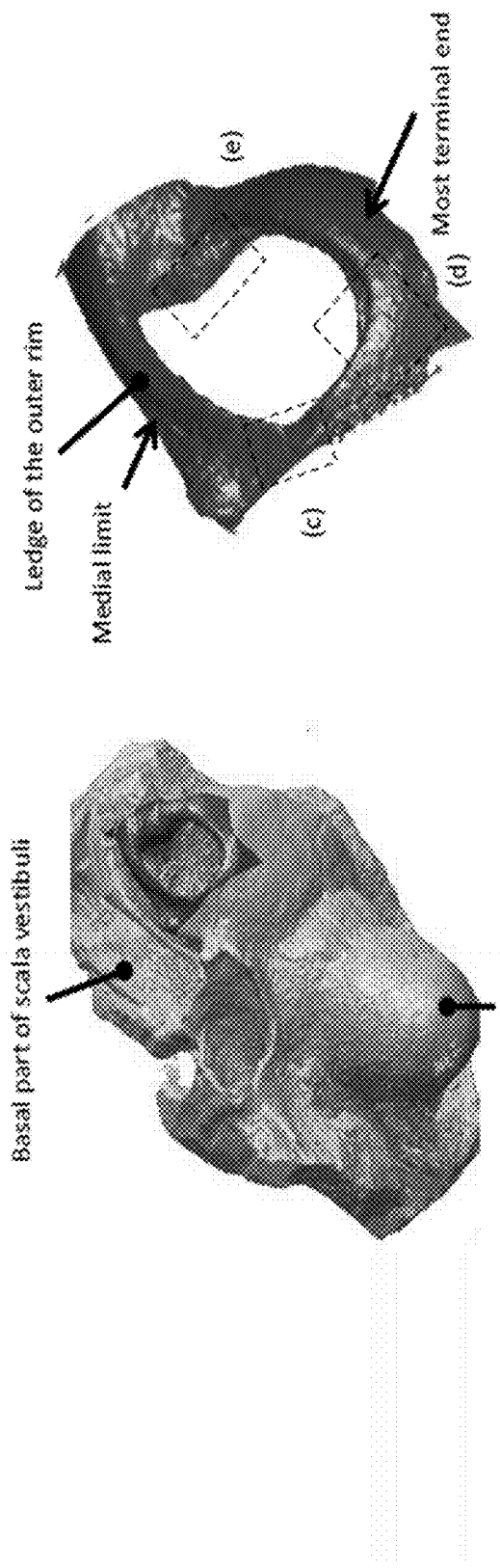
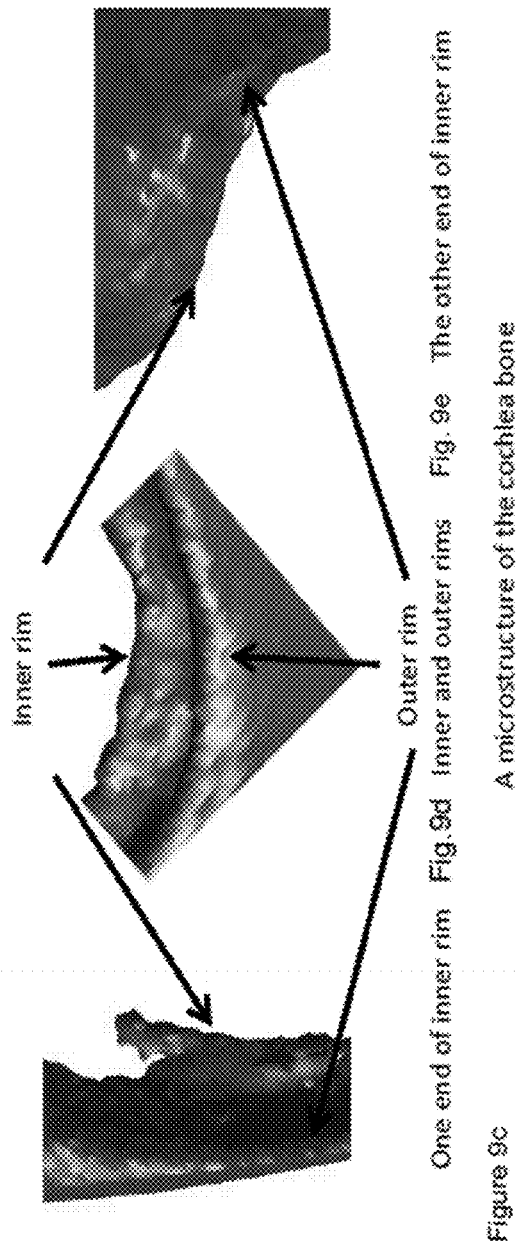
(a) A reconstructed bone of a cochlea
Figure 9a
(b) The terminal of the scala tympani
Figure 9b
One end of inner rim   Fig. 9d  Inner and outer rims   Fig. 9e   The other end of inner rim
Figure 9c          A microstructure of the cochlea bone

Figure 10 Scatter plots of Zygo scan data of a RWM and bone from three angles
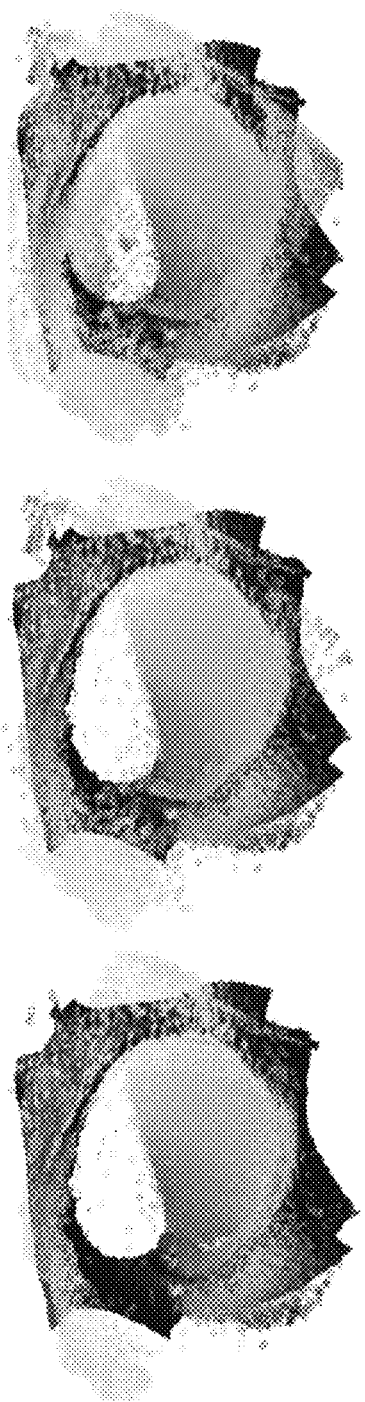
Figure 11 Images of serial stitching of three sets of Zygo scan data on µCT scan structure data
Figure 12 Comparison of µCT scan structure (left), single (middle) and triple (right) data

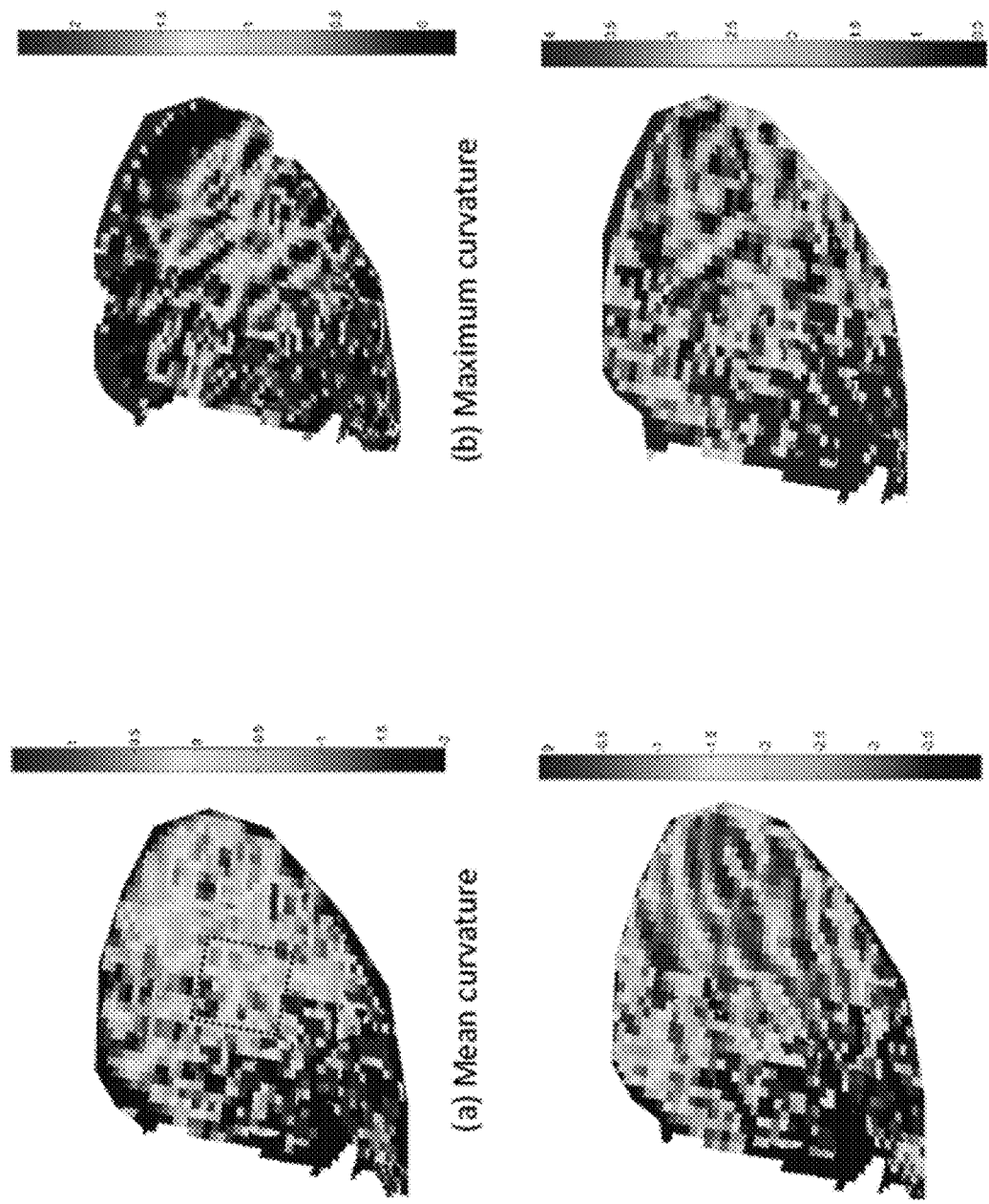
Figure 13 Contour graphs of the average, maximum, minimum curvatures and the difference between the maximum and minimum curvatures

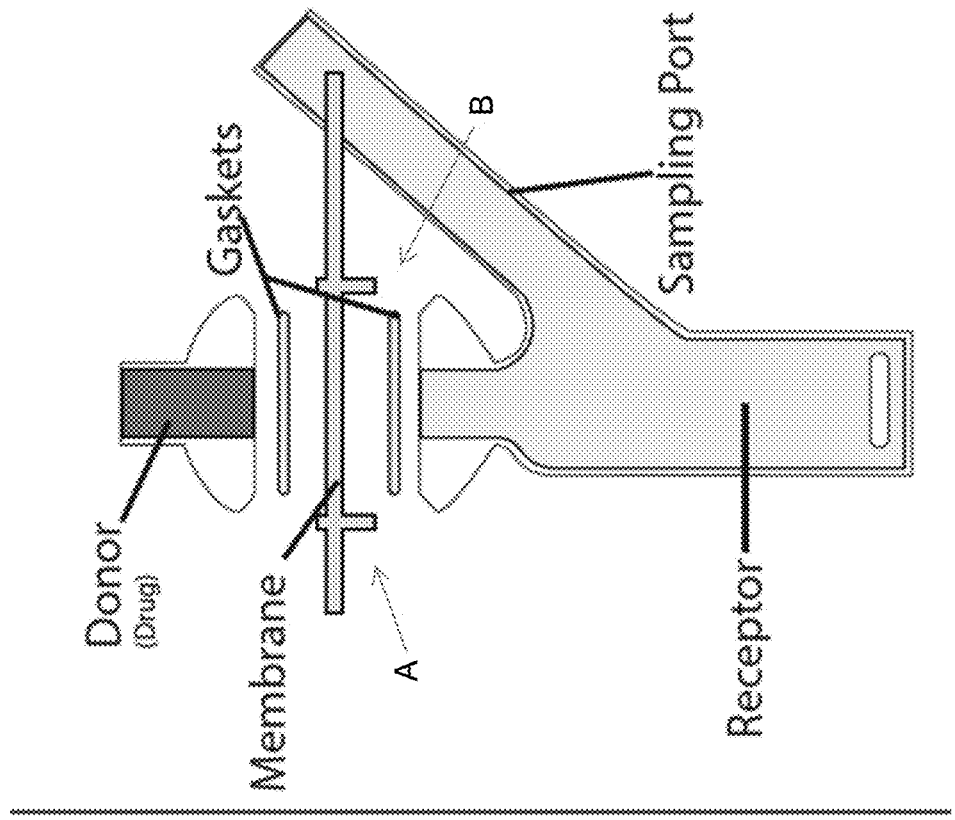
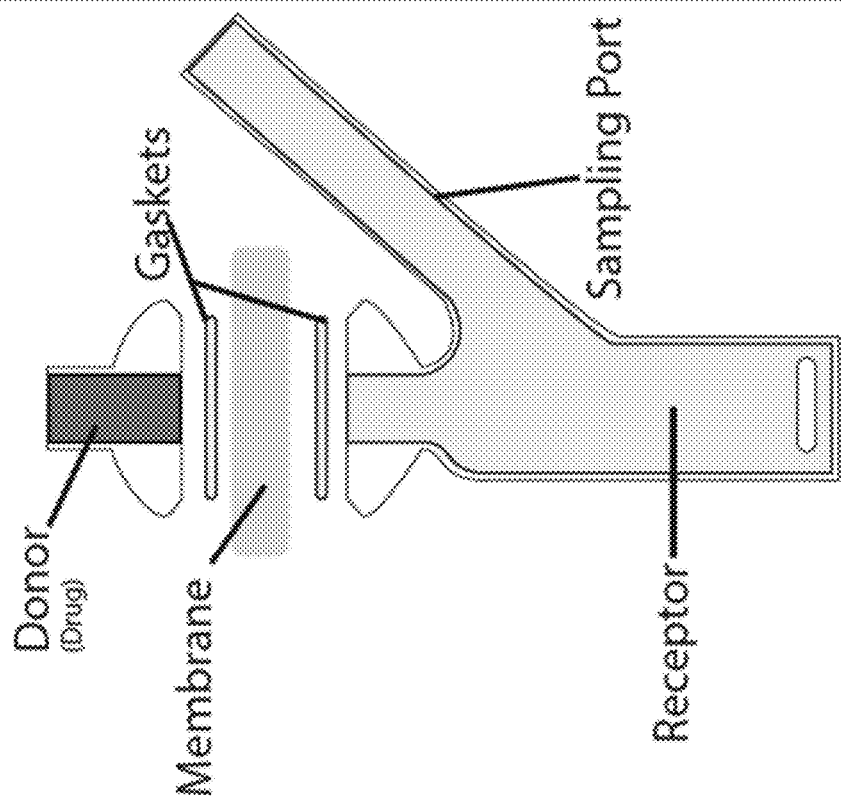
Figure 33B
Figure 33A

| Material in 1ml 1µM RhoB | Average Luminosity Exposure 1/500s | % ↓ RhoB Luminosity after 48 hours | Use in Method |
|---|---|---|---|
| Control | 87.94 | 0.00 | Control |
| Dental Dam (Latex) | 24.78 | 71.82 | Not usable |
| Latex | 18.17 | 79.34 | Not usable |
| Expanded PTFE | 84.91 | 3.45 | Gaskets |
| Silicon | 31.69 | 63.96 | Not usable |
| Acrylic | 83.78 | 4.73 | Adapter |
| BIS-GMA Composite | 87.66 | 0.32 | Embedding |

Figure 35

| | D (m²/s) | P_PORE (m/s) | P_RWM (m/s) | 1% perforation improvement |
|---|---|---|---|---|
| Gentamicin | 6.82 x 10⁻¹⁰ | 6.82 x 10⁻⁵ | 3.5 ± 4.6 x 10⁻⁸ | 1.9 ± 1.4 x 10 |
| Dexamethasone | 7.20 x 10⁻¹⁰ | 7.20 x 10⁻⁵ | 5.0~35.0 x 10⁻⁸ | 1.4~0.2 x 10 |
| TMPA | 1.01 x 10⁻⁹ | 1.01 x 10⁻⁴ | 1.9 x 10⁻⁸ | 5.30 x 10 |
| Rhodamine B (SALT) | 4.27 ± 0.04 x 10⁻¹⁰ | N/A | 2.4~8 x 10⁻⁸ | N/A |
| Rhodamine B | 4.27 ± 0.04 x 10⁻¹⁰ | 7.06 x 10⁻⁵ | 2.0 ± 1.0 x 10⁻⁸ | 3.5 x 10 |

Figure 36

SYSTEM AND METHOD TO LOCALLY DELIVER THERAPEUTIC AGENT TO INNER EAR

CROSS-REFERENCE TO RELATED APPLICATIONS

This application claims priority to U.S. Provisional Application No. 61/969,714 filed Mar. 24, 2014 and U.S. Provisional Application No. 61/981,458 filed Apr. 18, 2014. This application also claims priority to, and is filed as a Continuation-in-Part of U.S. PCT Application No. PCT/US13/75105 filed Dec. 13, 2013, which claims priority to U.S. Provisional Application No. 61/833,849 filed Jun. 11, 2013 and U.S. Provisional Application No. 61/737,285, filed Dec. 14, 2012, the contents of which are hereby incorporated by reference in their entirety.

BACKGROUND OF THE DISCLOSED SUBJECT MATTER

Field of the Disclosed Subject Matter

The disclosed subject matter relates to a drug delivery device and more specifically to a drug delivery system for the treatment of middle ear and/or inner ear disorders (e.g., Meniere's Disease, sudden sensorineural hearing loss and tinnitus).

Description of Related Art

Hearing loss is the most common sensory disturbance in humans affecting nearly 10% of the U.S. population. Balance disturbance and tinnitus are equally prevalent. In order to treat these disorders, it is often desirable to administer therapeutic agents, e.g., medications or other medical fluids, into the middle and inner ear of a patient (see FIG. 1). One known technique for administering such agents is intratympanic perfusion, as discussed in U.S. Pat. No. 7,840,260, the entirety of which is hereby incorporated by reference. Intratympanic delivery of drugs is typically accomplished by surgery. As shown in FIG. 2, the surgery involves making a small incision in the ear canal, i.e., anesthetized tympanic membrane (eardrum) and lifting the ear drum to create an access point to the middle ear, as shown in FIG. 3. Once the access is available, the medical provider inserts a needle or catheter into the middle ear, infusing the drug in liquid form and allowing it to be absorbed into the inner ear by diffusion across the round window membrane (RWM).

Other methods have included placing an incision or implanted tube in the tympanic membrane and then having the patient self-dispense the drug into the external ear canal whereby it is intended to pass through the opening into the middle ear, and thence the inner ear.

These conventional techniques have many disadvantages. Many therapeutics are not capable of diffusing across the RWM due to their size or molecular weight. Further infectious debris can be carried into the middle ear from the external canal, with the risk of creating a middle ear infection, and passage of the liquid into the middle ear is inhibited by the surface tension of the liquid.

Protected by one of the hardest bones in body, the cochlea is a nearly impenetrable structure frustrating both bacteria and clinicians trying to gain access to it. Consequently, means for reliable delivery of agents into the inner ear for therapeutic purposes remains a formidable challenge. Were it not for its oval and round "windows", delivery of therapeutic agents to the inner ear would always necessitate traumatic disruption of its bony walls with fearful consequences to hearing. Thus, the RWM is an attractive target for intracochlear delivery of drugs or biologic agents as it can avoid traumatic disruption of bony walls of the cochlea with fearful consequences to hearing. However, to date there is no product available that is capable of controlled penetration of the RWM to allow local delivery of therapeutic agent into the inner ear. Rather, commercial products that once existed to locally deliver a drug proximally adjacent to the RWM solely relied on diffusion across the membrane for treatment. However, these commercial products have been largely abandoned as they have not dependably delivered material into the cochlea. Moreover, simple diffusion of drugs or agents across the RWM is limited by the type of material suitable for delivery, e.g., size of material to be delivered, difficulty with precise dosing, timing, and precision of delivery over time.

For example, transtympanic therapy with gentamicin and steroids is an important part of therapeutic armamentarium for the treatment of Meniere's disease. However, transtympanic therapy is associated with significant variability in clinical response and toxicity that is in large part related to the variable intracochlear bioavailability of the drug.

Thus, there remains a need for an apparatus and corresponding method that facilitate local delivery of therapeutic agents to the inner ear for reliable and predictable intracochlear delivery without anatomic or functional damage.

SUMMARY OF THE DISCLOSED SUBJECT MATTER

In one aspect of the disclosed subject matter, a medical device capable of creating temporary perforations in the round window membrane of an inner ear is provided. The medical device includes a plurality of micro-needles having a diameter of about 10 micron. The size of the micro-needles enables the micro-needle to penetrate the round window membrane of the inner ear to create temporary, self-closing perforations. The temporary perforations allow access to the inner ear for local drug delivery of therapeutic agents. The plurality of micro-needles is coupled to a base, which is configured to physically engage a driver device. Thus, both the medical device and the driver can be separate components that are engageable to each other to define a modular system.

The micro-needles may be hollow or solid, made of silicon or a more rigid material (e.g. tungsten) and can be configured with a taper along its length. The taper may be a gradual taper such as a gradual decrease in diameter along the length of the micro-needle, or a stepped taper with abrupt changes in diameter that serve as reinforcing ribs or ledges. The micro-needles may be arranged in a regular pattern such as in an ordered array or disordered in a random pattern. In one embodiment, the micro needles are arranged in an array, for example a 10 by 10 array. The size of the array however will be dependent on the desired dosage of therapeutic agent. For example, the consistent delivery of therapeutic agent through the lumen within the hollow micro-needles by a 10 by 10 array provides a dosage of therapeutic agent that is double the amount delivered by a 5 by 5 array, and so on. Additionally or alternatively, the therapeutic agent can be disposed on an exterior surface of a solid micro-needle.

In another embodiment a system for delivering therapeutic agent to the inner ear of a subject is provided which comprises an instrument for accessing the round window membrane; a plurality of micro-needles, each micro-needle having a diameter of about 20 microns with sufficient rigidity to perforate the round window membrane; and a driver, wherein the plurality of micro-needles is coupled to the driver. In some applications, the micro-needles is removed from the round window membrane perforation prior to dispensing the therapeutic agent.

In another embodiment a method of delivering a therapeutic agent into the cochlea is provided which comprises determining the shape of at least one micro-needle; determining the amount of force to be applied to the at least one micro-needle for perforating the round window membrane; determining the displacement and indentation rate of the at least one micro-needle; positioning the at least one micro-needle proximate the round window membrane; perforating the round window membrane; and dispensing a therapeutic agent at said perforation(s).

In another embodiment, the system further includes an indicator disposed along the system, such as a sensor, to indicate when the RWM is fully penetrated by the micro-needles. For example and not limitation, a sensor may be included that is capable of sensing penetration into fluid. The sensing of penetration into fluid indicates that the RWM is fully penetrated.

In another embodiment, the system further includes an aspirating lumen within at least one micro-needle which is connected to a suction device, e.g. pump. With respect to the aspirating lumen, fluid from the middle or inner ear can be aspirated before, during or after local delivery of therapeutic agent. The system and components can be disposable, single-use products.

Thus, described herein is a medical device and system for delivering a therapeutic agent into the cochlea comprising an instrument for accessing the round window membrane, at least one micro-needle, the at least micro-needle having sufficient rigidity to perforate the round membrane, and a delivery mechanism for dispensing a therapeutic agent at said perforation(s).

In accordance with another aspect of the disclosed subject matter, a method of delivering a therapeutic agent into the cochlea is disclosed which comprises providing at least one micro-needle on an instrument, positioning the at least one micro-needle within the inner ear, perforating the round window membrane, and dispensing a therapeutic agent at said perforation(s). In some embodiments, the at least one micro-needle is removed prior to dispensing.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIGS. 9 (a) to 9(e) are images of the microstructure of the inner ear and the terminal of the scala tympani.

FIG. 10 are scatter plots of Zygo scan data of a cochlea sample showing the topographies of a RWM and the bony terminal end of the scala tympani.

FIG. 11 is a set of Zygo scan data were stitched on the surface of the reconstructed bone surface measured by one μCT scan.

FIG. 12 Structure acquired with μCT (left), single (middle), and three Zygo scan data are compared from another angle.

FIG. 13 shows the mean (a), maximum (b), minimum (c), and the difference between the maximum and minimum curvatures (d) were plotted as contour graphs. The rectangle drawn with a broken line in FIG. 13(a) shows the area that was used to calculate the average and standard deviation of each 2-D array of data

FIGS. 30 and 33A-B are an exemplary illustrations of a Franz™ Cell for studying transdermal drug delivery.

FIGS. 35-36 are charts of exemplary data in accordance with the present disclosure.

DETAILED DESCRIPTION OF EXEMPLARY EMBODIMENTS

The methods and systems presented herein relates to a system for treatment of the middle ear and/or inner ear disorders, and includes an apparatus and method for the compact, selectively controlled and metered introduction of a medical fluid, such as a drug, into the inner ear of a patient. Particularly, the presently disclosed subject matter is directed towards an apparatus having a plurality of micro-needles for creating temporary perforations in the round window membrane which allow for reliable and predictable intracochlear delivery without permanent anatomic or functional damage.

Figure 1:
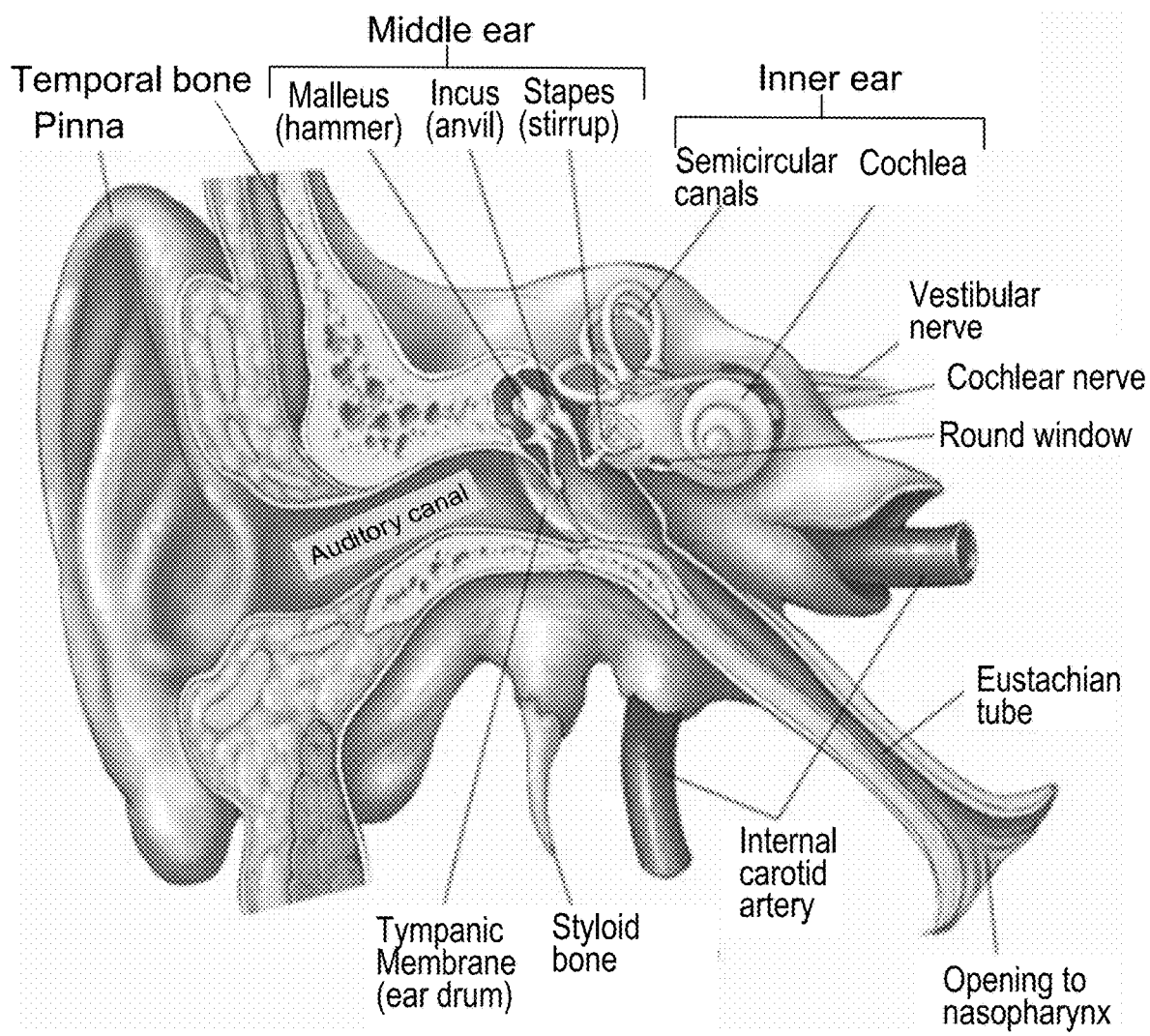
FIG. 1 is a schematic representation of the ear anatomy.
Figure 2:
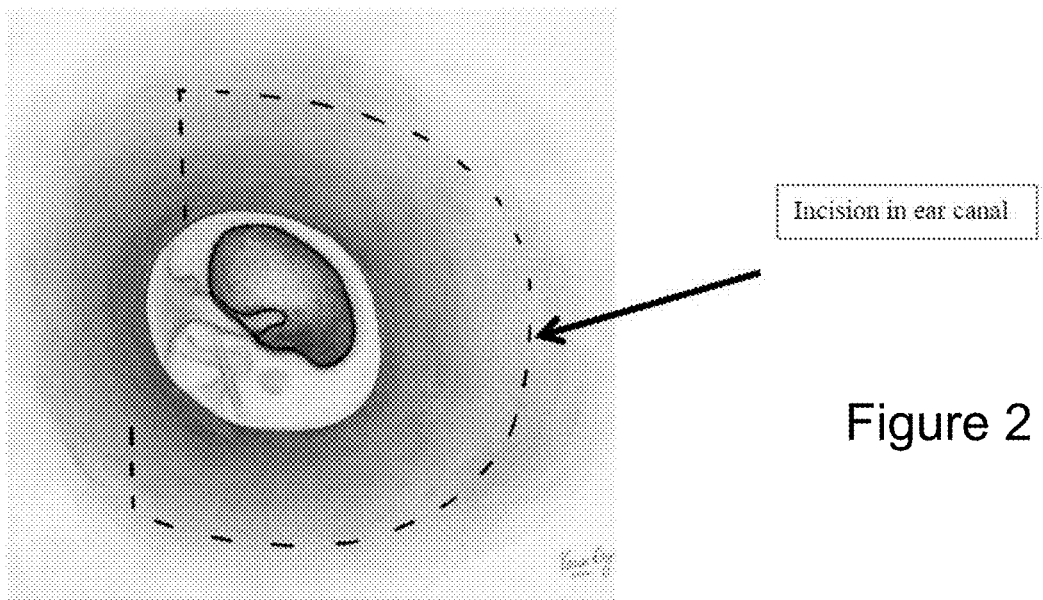
FIG. 2 is a schematic representation of an incision made in the ear canal.
Figure 3:
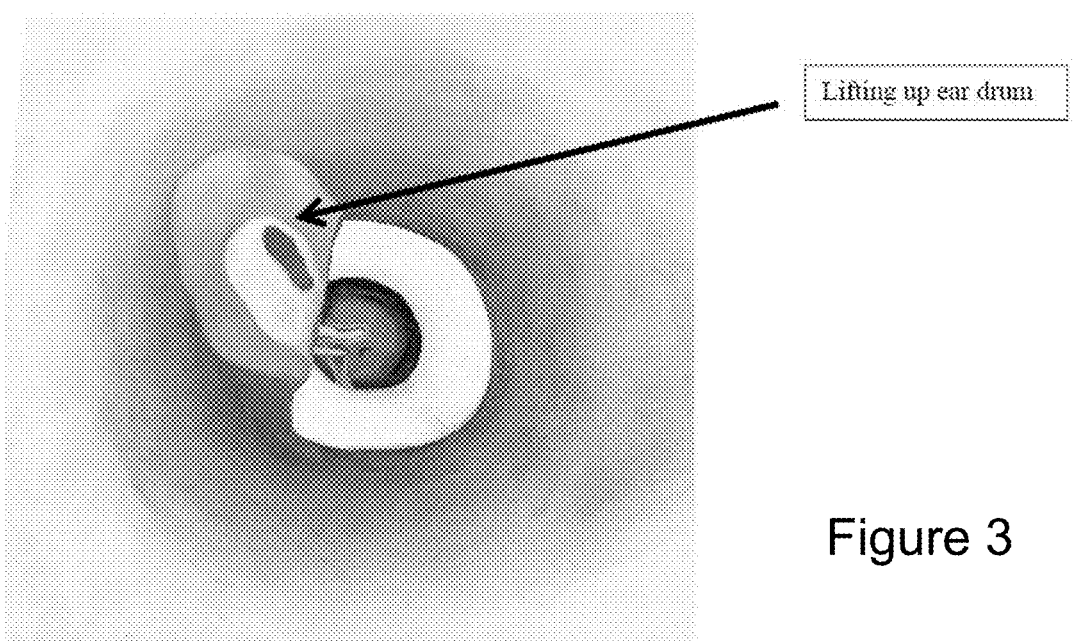
FIG. 3 is a schematic representation of the lifting of the ear drum cut along the incision shown in FIG. 2 in order to gain access to the middle ear.

As shown in FIG. 1, the anatomy of the ear includes a middle ear comprising the hammer, anvil, and stirrup bones, and an inner ear comprising the semicircular canals and cochlea. The middle ear and inner ear have barriers to entry and are separated from auditory canal by the tympanic membrane or ear drum. Moreover, the inner ear is further protected from entry by its almost impenetrable structure. The round window membrane (secondary tympanic membrane) disposed at the inner ear provides an avenue to permit local delivery of therapeutic agents directly to the innerear.

Round Window Membrane.

The Round Window Membrane (RWM) is a three layered structure designed to protect the inner ear from middle ear pathology and facilitate active transport. There is an outer epithelial layer that faces the middle ear, a central connective tissue layer, and an inner epithelial layer interfacing with the scala tympani. The most prominent feature of the outer epithelial layer is the extensive interdigitations and tight junctions of its cells; in addition, there is also a continuous basement membrane layer. This architecture with tight junctions and a continuous basement membrane functions as a defensive shield designed to protect the inner ear from middle ear infections. The connective tissue core contains fibroblasts, collagen, and elastic fibers, and houses blood and lymph vessels. The connective tissue is divided roughly into thirds differing in fiber type and density thus essentially establishing a gradient. This layer is responsible for providing compliance to the RWM. Finally, there is a discontinuous inner epithelial layer that bathes in the perilymph of the scala tympani. As previously noted, conventional transtympanic delivery is limited as it relies on the ability of particles to diffuse or be actively transported across this three layered membrane.

A large range of materials are able to cross the RWM, including various antimicrobials, steroids, anesthetics, tracers, albumin, horseradish peroxidase, latex spheres, germicidal solutions, water, ions, and macromolecules (including bacterial toxins) as long as the materials are suitable for simple diffusion transport. Several factors contribute to the RWM permeability, including size, charge, liposolubility, the morphology of the compound, and the thickness of the RWM. Size has proven to be a factor in permeability, as 1 μm microspheres cross the RWM, but 3 μm microspheres cannot. Furthermore, substances with a molecular weight of less than 1000 kDa diffuse across the RWM fairly rapidly, whereas substances over 1000 kDa require pinocytosis to cross the RWM. Charge of the molecule can also impact its ability to traverse the RWM; for example, it has been noted that cationic ferratin crosses the RWM, but anionic ferratin does not. Finally, increased thickness of the RWM will decrease permeability of substances. While the average thickness of the human RWM is between 70 and 80 μm, this thickness can double in inflammatory conditions. RWM permeability can be altered with the use of exogenous adjuvants such as histamine (for its vasodilatory effects), hyaluronic acid (for its proposed osmotic effect), and dimethylsulfoxide (for its ability to increase medication solubility in perilymph); however, their clinical applications are limited. Consequently, a major limitation of conventional transtympanic delivery method that takes advantage of this natural permeability of the RWM is the great variability in intracochlear delivery of the therapeutic agent; this leads to variation in clinical response and toxicity. Furthermore, many therapeutics cannot be delivered due to the molecular size and weight. The systems and methods described below provide a solution to the problem of local drug delivery to the inner ear, and is not limited by factors required for simple diffusion.

In accordance with an aspect of the disclosed subject matter, the mechanical properties of the RWM were characterized using a nanoindenter, as discussed in further detail below.

Micro-Needles to Create Micro-Perforation of RWM.

To overcome the limitations of diffusion based delivery across RWM, the present embodiments create controlled micro-perforations through the RWM with a plurality of micro-needles that: 1) improves the diffusive permeability of RWM dramatically and controllably; 2) minimizes the damage to the RWM cellular architecture so that RWM heals itself; 3) prevents the convective perilymph leak by the cerebrospinal fluid (CSF) pressure and prevent unintended disruption of endocochlear pressure fluctuation, and 4) locally delivers drugs or compounds that cannot diffuse across the RWM.

In accordance with an aspect of the disclosed subject matter, a device capable of locally delivering a therapeutic agent into the inner ear or cochlea is provided. The device includes a plurality of micro-needles configured to controllably penetrate (to a desired depth) the RWM to create temporary access to the inner ear through temporary perforations. The plurality of micro-needles may have a regular or ordered arrangement such as in an array, or have an irregular or random arrangement, if so desired.

The micro-needles are suitably sized to create temporary perforations in the RWM without tearing or ripping the RWM. The term "controlled penetration" or "controlled perforation" means that the opening created by the micro-needle has substantially regular or smooth edges, as opposed to a "tear" or "rip" which is to pull apart in a way that leaves ragged or irregular edges. The aperture created upon insertion of the micro-needle does not expand or distort, but instead retains a shape and size which corresponds to the shape and size of the micro-needle which created the aperture. The term "temporary perforations" means that the openings created by the micro-needles self closes without the need for a wound closure procedure. In this regard, in one embodiment the micro-needles have a diameter of about 10 micron. As discussed in further detail herein, it has been found that the size of the micro-needle is important to create perforations or openings in the RWM that self-close. The creation of temporary perforations in the RWM allows for reliable and predictable intracochlear drug delivery without permanent anatomic or functional damage to the ear.

Figure 6:
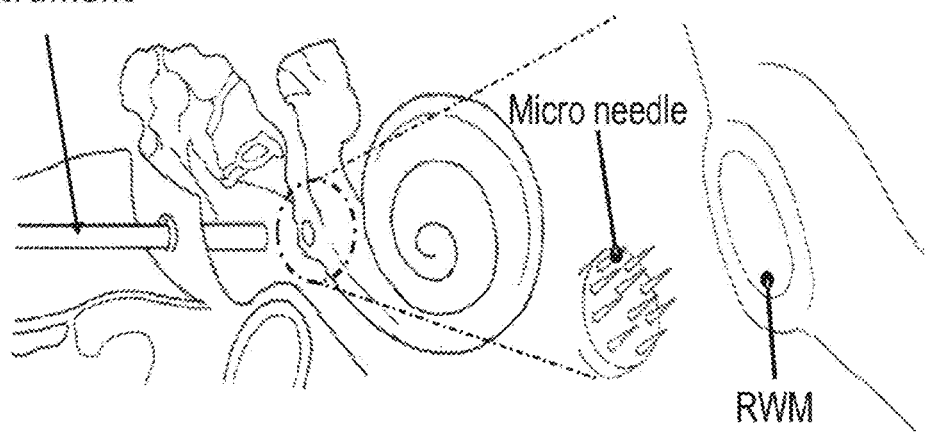
FIG. 6 is a schematic representation of an exemplary device having a plurality of micro-needles and coupled to a delivery device in accordance with one embodiment of the disclosed subject matter.
Figure 42A:
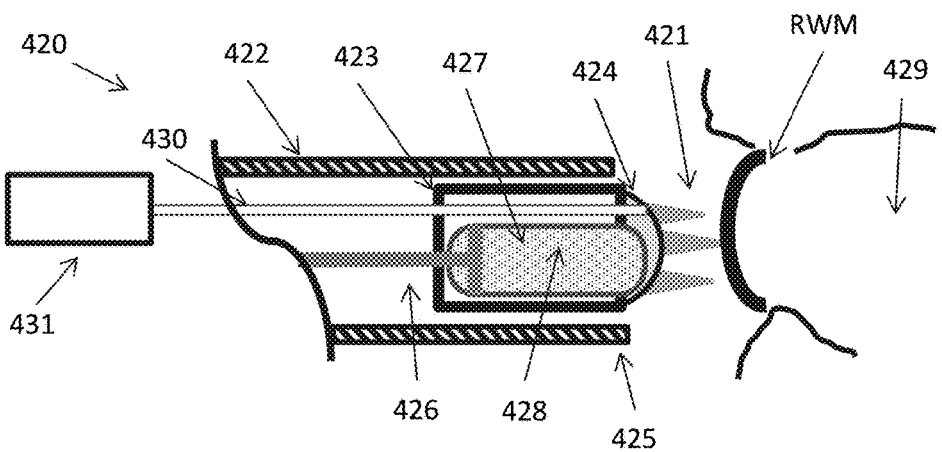
FIGS. 42A-42C show in schematic cross-sections the operation of a system for delivering therapeutic agent to an inner ear of a subject according to an embodiment described herein.
Figure 42B:
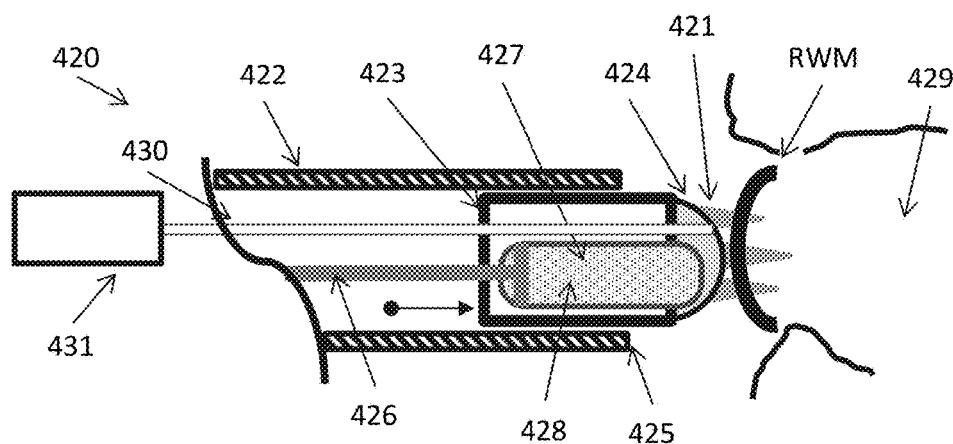
Figure 42C:
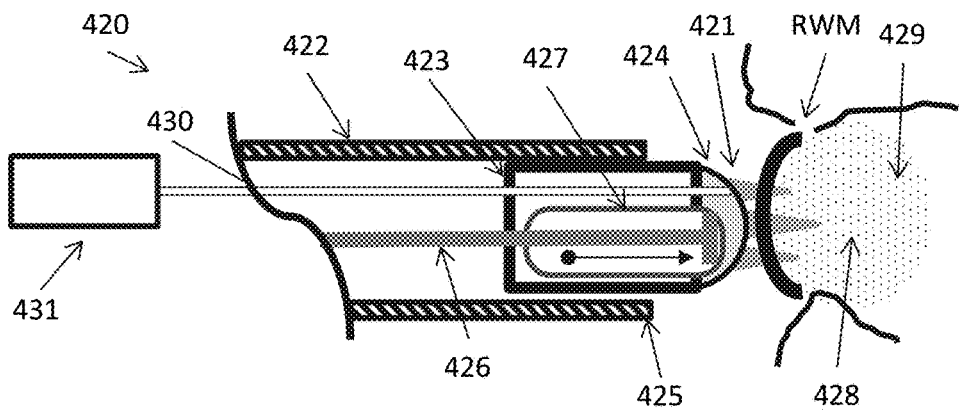

The micro-needles can be formed with either a solid or hollow construction. The hollow configuration permits drug delivery through a lumen within the micro-needle to the inner ear. For example, the array of micro-needles can be connected to an osmotic pump (or syringe) which is in fluid communication with a reservoir housing the therapeutic agent, and subsequently mounted onto a surgical instrument (e.g. catheter or introducer) that allows access to the RWM either via the tympanic membrane or via the mastoid process. FIGS. 42A-42C show schematically the operation of a system 420 for delivering therapeutic agent to an inner ear of a subject comprising: a plurality of micro-needles 421; an instrument 422 for accessing a round window membrane (RWM) via the tympanic membrane or the mastoid process, thereby positioning the plurality of micro-needles 421 proximate the round window membrane; and a driver 423 that operates to insert the micro-needles 421 into the round window membrane to create the perforations to the desired depth, wherein the plurality of micro-needles 421 is coupled to the driver 423. The features in the drawings are not drawn to scale, but are illustrative of their function. Each micro-needle has sufficient rigidity to perforate the round window membrane. The plurality of micro-needles 421 is provided as an array on a base 424 that is coupled to the driver mounted at the distal end 425 of the surgical instrument 422, as described in more detail below. In the embodiment shown, the base is configured as a portion of an osculating sphere with a radius equal to the curvature radius of the round window membrane along its minor axis. The surgical instrument 422 (e.g. catheter or introducer) allows access to the RWM either via the tympanic membrane or via the mastoid process, as shown in FIG. 6. The surgical instrument 422 positions the micro-needles 421 proximate the RWM as shown in FIG. 42A. Once the micro-needles are positioned proximate the RWM, the driver 423 can operate to insert the micro-needles into the RWM to create the perforations to the desired depth, as shown in FIG. 42B. As discussed in greater detail below, the driver 423 advances the microneedle array in the direction indicated by the arrow over a distance sufficient to create the perforations to the desired depth while maximizing the energy transfer efficacy to the perilymph fluid and minimizing the stress within the RWM. In some embodiments as illustrated in FIG. 42C, upon creation of the perforations, the array of hollow micro-needles 421 will not be removed. Instead they will remain in the RWM and serve as a conduit to inject therapeutics at a controllable rate through the hollow micro-needles 421, and into the RWM, or distal the RWM as desired. As shown schematically in FIG. 42C, the osmotic pump or syringe 426 advances in the direction indicated by the arrow to expel the therapeutic agent 428 from the reservoir and into, for example, the inner ear 429 distal of the RWM. Alternatively, the micro-needles can be retracted from the perforations formed in the RWM by reversing the driver back to the position shown in FIG. 42A, and thereafter a therapeutic material can be delivered and dispensed from the micro-needles at a location proximate the perforations and pass through the perforations into the inner ear 429. FIGS. 42A-42C also show an aspiration lumen 430 in fluid communication with a lumen within a hollow micro-needle, and in fluid communication with a suction device 431 such as a pump.

In embodiments which employ a solid micro-needle construction, the micro-needle(s) can be coated with a therapeutic material to permit local delivery of the therapeutic material into the inner ear. Alternatively, the micro-needles can be used to completely penetrate through the RWM to allow drug delivery to the inner ear via another device such as a syringe. Accordingly, the micro-needles can either create temporary micro-perforations that facilitate diffusion to provide consistent intracochlear delivery, or can be used for direct injections into the cochlea.

Figure 4:
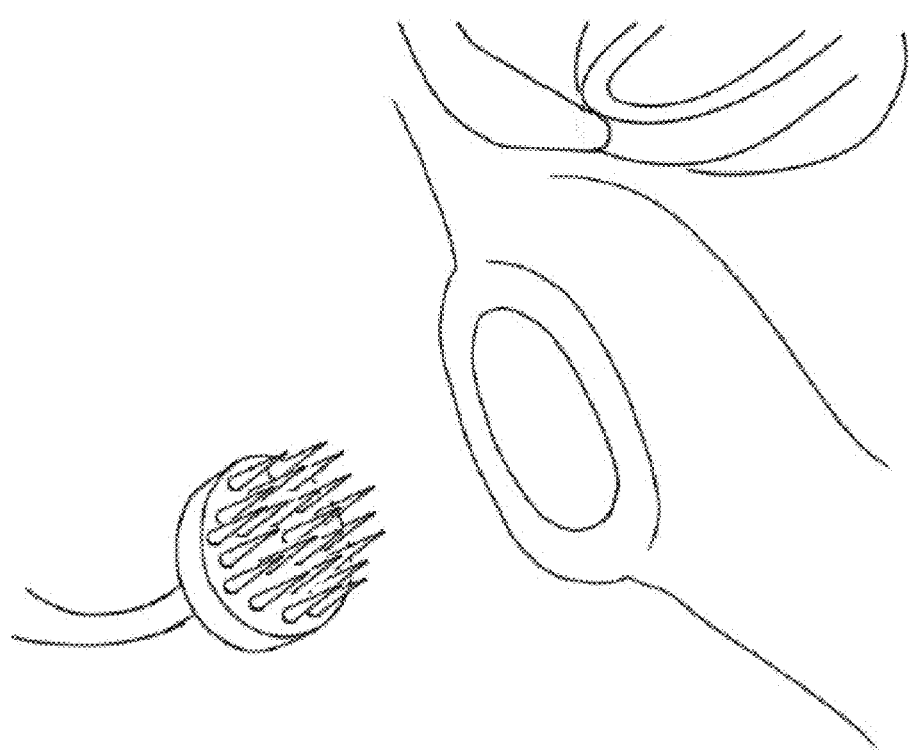
FIG. 4 is a schematic representation of an exemplary device having a plurality of micro-needles in accordance with one embodiment of the disclosed subject matter.
Figure 5:
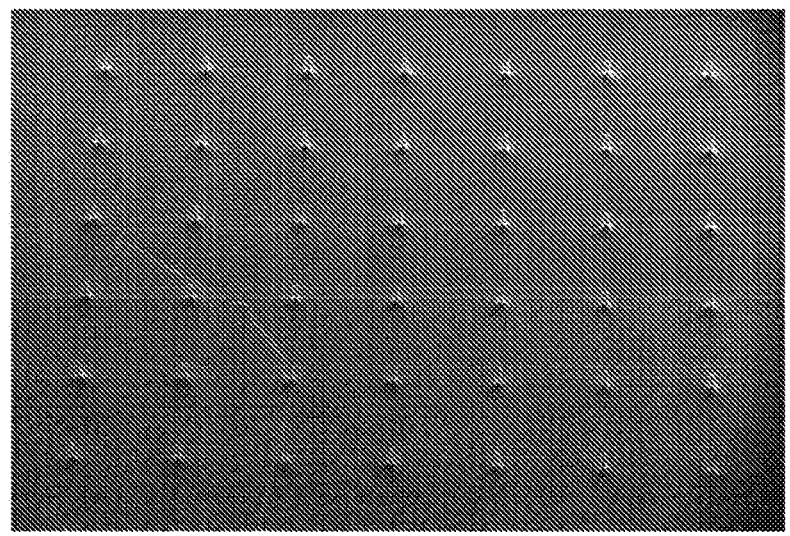
FIG. 5 is a schematic representation of one embodiment of the plurality of micro-needles in the form of an array of micro-needles.
Figure 7:
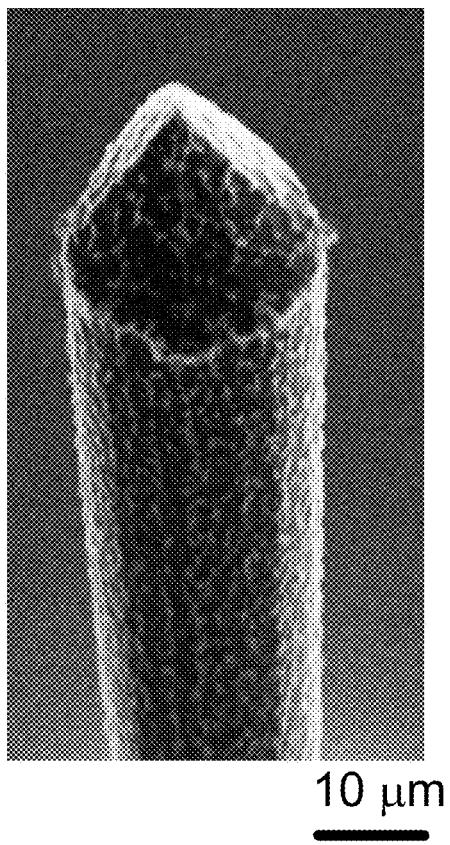
FIGS. 7-8 depict exemplary embodiments of a silicon and tungsten micro-needle in accordance with the disclosed subject matter.
Figure 8:
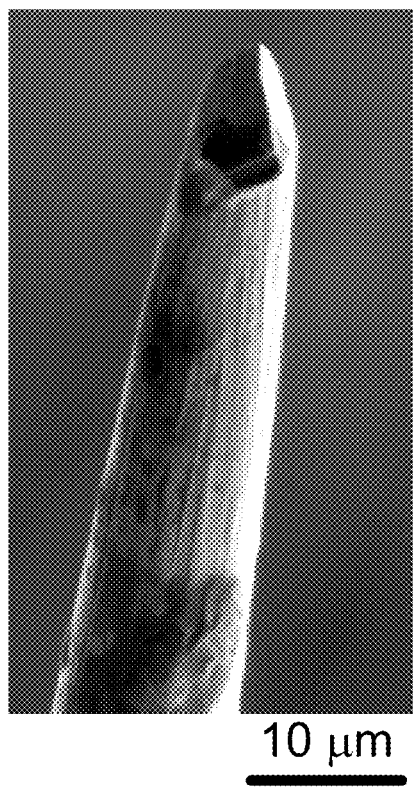

The plurality of micro-needles can be a component device that is configured to engage a surgical instrument for introduction into the ear, such as a driver, introducer, catheter, or other device. In this regard, the device includes a base and a plurality of micro-needles. The base is adapted to mount onto a surgical instrument that allows access to the RWM either via the tympanic membrane or via the mastoid process. In this regard, the base can include threads to screw onto the surgical instrument. However, other structures for physical coupling to the surgical instrument can be employed as would be known to one of skill in the art, such as clips, snap-on friction fit engagement, and the like. Exemplary embodiments of the medical device are depicted in FIGS. 4-6 which illustrate both a circular (FIGS. 4 and 6) array and polygonal array (FIG. 5) of micro-needles. Similarly, FIGS. 7 and 8 depict magnified views of a tungsten and silicon micro-needles, respectively.

Figure 43:
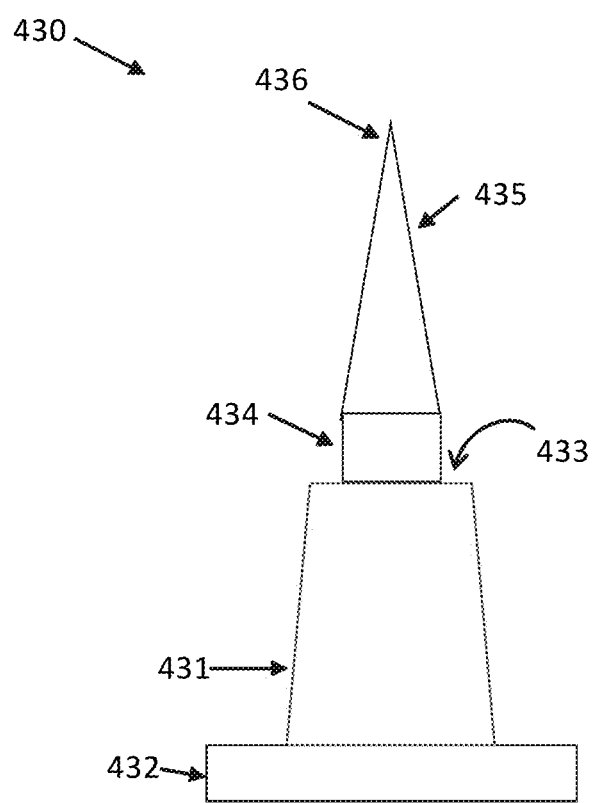
FIG. 43 shows schematically a profile of a microneedle with a stepped taper according to an embodiment of the disclosed subject matter.

For purposes of illustration and not limitation, the micro-needle of the present disclosure can be formed with a 0.5 µm tip, and a 20 µm diameter shaft which is 100 µm in length. Such a micro-needle exhibits a 0.4~5 mN rupture force, a buckling load of 160 mN, with a safety margin of greater than 30, as described in further detail below. The micro-needle can be formed with a gradual or stepped taper at the distal tip. The stepped taper configuration results in abrupt changed in diameter which can serve as structural reinforcing ridges for withstanding greater insertion loads without buckling or deforming. An embodiment of a microneedle with a stepped taper is shown schematically in FIG. 43 (not to scale), in which the proximal portion 431 of the microneedle 430, having a gradual taper (as shown, with constant reduction in diameter), is attached to a base 432. An abrupt change in taper (as shown, the diameter of the microneedle shaft is reduced abruptly at 433) provides a ledge on the microneedle 430. The shaft of the microneedle has a constant (reduced) diameter for a middle portion 434 and the distal portion 435 resumes a gradual taper to the microneedle tip 436. The ledge at 433 may provide a stop that engages the proximal surface of the membrane to limit penetration of the microneedle into the membrane. It may also serve as a reinforcement that engages with the proximal surface of the membrane to stabilize the position of the microneedle relative to the membrane. Additionally, or alternatively, the desired strength characteristics of the micro-needle can be achieved by selection of the material properties (e.g. tungsten vs. silicon).

The surgical instrument can be configured for pediatric indication or adult indication. For example, the length and diameter of the surgical instrument can be smaller for use for pediatric treatment.

In some embodiments each micro-needle can be formed with a uniform geometry such that each corresponding perforation is a uniform and constant depth. Additionally, or alternatively, select micro-needles can be formed with differing geometries to provide a non-uniform or patterned perforation design. Furthermore, a greater concentration of micro-needles can be provided at one portion of the RWM than another to provide the operator with greater flexibility and customization for different patients. Moreover, the micro-needles can be formed with differing lengths which coincide or map to the contour of the RWM so as to ensure a uniform depth of insertion into the RWM across its varying or non-planar (i.e. "saddle point") shape, as described in further detail below.

The micro-needle arrays disclosed herein are designed for painless transdermal administration of drugs, which can be delivered through a lumen within a hollow micro-needle, or coated on the exterior of a solid micro-needle. The size of the needle can be varied greatly depending on the tissue and the material to be injected. The micro-needles can be formed from a variety of metals and polymers that are bio-compatible/degradable. In an exemplary embodiment, the micro-needles are formed of silicon due to its relative ease of manufacture. In alternative embodiments, the micro-needles can be formed of more rigid materials (e.g. tungsten) which allow for greater loading without buckling of deformation. The application of micro-needle arrays to RWM can serve as an agile method for intracochlear delivery.

In another aspect, the subject matter provides an apparatus including the plurality of micro-needles and driver formed as a unitary or non-separable device which can be disposable or reusable.

In another embodiment, the system or apparatus further includes an indicator to signal full penetration through the RWM. In this regard, the system or device may include a sensor to sense air, tissue, and/or fluid. Once the sensor senses fluid the sensor communicates with the indicator to signal full penetration through the RWM.

In yet another aspect, the system or apparatus may include an aspiration lumen and aspirator device. In this regard, the aspirator can aspirate fluid from the middle or inner ear, and deliver drugs locally to the middle or inner ear.

In accordance with another aspect of the present disclosure, the method of determining the shape of at least one micro-needle, the amount of force to be applied to the micro-needle for perforating the round window membrane, and determining the displacement and indentation rate of the micro-needle is also provided, as described in the various studies outlined below.

Changes in Diffusion with Micro-Perforations.

In accordance with another aspect of the disclosure, permeability of the RWM is determined by the biological conduits—extracellular milieu or picocytosis—and experimentally, those of therapeutic reagents determined in the guinea pig model disclosed herein are moderate and highly variable (Dexamethasone: $3.5 \pm 4.6 \times 10^{-8}$ m/s; Gentamicin: 5.0 $35.0 \times 10^{-8}$ m/s; TMPA; $1.9 \times 10^{-8}$ (m/s)). On the other hand, diffusion of therapeutic reagent across the RWM can be modified by introduction of micro-perforations. From Fick's first law, diffusion is described by $$J = -D\nabla\phi \quad (1)$$

where J is diffusion flux in $mol/m^2 \cdot s$, D is the diffusion coefficient in $m^2/s$, and $\phi$ is the concentration in mol/l. Then from a one-dimensional simplification of the pore $$\frac{\partial \phi}{\partial y} = 0, \frac{\partial \phi}{\partial z} = 0 \therefore \nabla\phi = \frac{\partial \phi}{\partial x}. \quad (2)$$

This can be further simplified with the gradient is uniform across the pore to obtain $$\frac{\partial \phi}{\partial x} = \frac{c_1 - c_0}{h}, \therefore J = -D\frac{c_1 - c_0}{h} \quad (3)$$

where x is the axis through the pore in m, cx is the concentration at both ends in mol/l, and h is the RWM thickness in m. Then from the definition of flux $$Flux = \int_s J \, dS = -DA\frac{c_1 - c_0}{h} = -\frac{D}{h}A(c_1 - c_0) \quad (4)$$

the permeability of the membrane is $$Flux = -PA(c_1 - c_0) \quad (5)$$

where P=D/h is the permeability in m/s.

Thus the permeability of one pore can be estimated from the diffusion coefficient and the thickness of the membrane (10 μm, guinea pig). As seen in Table 1, the improvement ratio with 1% area perforation (made with micro-needle array) is shown below: a 1% area modification leads to 14 to 50 fold increase in diffusion.

TABLE 1

Permeabilities of pores and RWM for various medications

|  | D (m2/s) | $P_{pore}$ (m/s) | $P_{RWM}$ (m/s) | 1% perforation improvement |
|---|---|---|---|---|
| Gentamicin | $6.82 \times 10^{-10}$ | $6.82 \times 10^{-5}$ | $3.5 \pm 4.6 \times 10^{-8}$ | $1.9 \pm 1.4 \times 10$ |
| Dex. | $7.20 \times 10^{-10}$ | $7.20 \times 10^{-5}$ | $5.0 \sim 35.0 \times 10^{-8}$ | $1.4 \sim 0.2 \times 10$ |
| TMPA | $1.01 \times 10^{-9}$ | $1.01 \times 10^{-4}$ | $1.9 \times 10^{-8}$ | $5.30 \times 10$ |

A potential concern of introducing pores within the RWM is leakage of perilymph from the scala tympani into the middle ear. The possibility of perilymph leakage can be mitigated by controlling the pore size, which in turn, is determined by the size of needle used. Decreasing the diameter of a pore prevents leakage of perilymph without slowing the diffusive transport of therapeutic reagents. In smaller pores, the viscous resistance to motion of the fluid due to the close presence of the walls of the pore causes a decrease in the flow rate. More precisely, the Reynolds number, which is the ratio of the inertial forces to the viscous forces in the flowing fluid, can classify this behavior. The small Reynolds number due to large viscous forces lead to a laminar, rather than a turbulent, flow of liquid through the pore. Under such circumstances, the fluidic resistance of a circular pore is inversely proportional to the 4th power of the pore diameter.

Thus decreasing a pore diameter by a factor of 10 while increasing the number of the holes by 100 times to keep the total area constant, increases the fluidic resistance 100 times.

In one embodiment, the plurality of micro-needles are a 10 by 10 array of micro-needles. However, other embodiments can be used such as a 5 by 5 array of micro-needles or a 20 by 20 array of micro-needles. The selection of the particular array configuration can depend on desired dosage of therapeutic agent. Accordingly, in some embodiments, a kit can be provided that includes a multiple devices comprising a base and a plurality of micro-needles in different sizes which would correspond to different dosages. For the purpose of illustration and not limitation, the kit can include one or more devices including micro-needles arranged in a 5 by 5 array, or a 2 by 2 array, or a 10 by 10 array. Each of the devices include a base configured to couple to a driver. In some kits a single universal base can be provided which can be coupled to each of the different arrays of micro-needles.

The Driver

In accordance with another aspect of the disclosure, the geometrical relationship of the driver design with respect to the topography of the RWM provides for an improved driver design. The transducer tip diameter and the surgical method of coupling to the RWM are known to have significant effects on performance of the RWM driver. For example, a chinchilla model was developed to study the performance variables in vivo. However, no detailed theoretical model regarding the physics exists to validate the experimental model and to evaluate the energy transfer efficacy. One vital element to develop such a theoretical model is quantified structure data of the RWM and RW niche (RWN). After the anatomy of the RW was described qualitatively, a quantitative study of the RWM dubbed the concave and convex surface structure of the RWM as a mathematical "Saddle Point" (or perhaps more commonly, "Pringles® potato chip,"). However, in these studies, magnetic resonance imaging (MRI) microscopy studies had insufficient resolution to characterize typical rodent RWMs and a histological technique had sufficient resolution but lacked accuracy. Moreover, both techniques require the specimen to undergo biochemical and mechanical processing, which raises uncertainties with regard to deformation and stress within the RWM. Accordingly, one feature of the present disclosure develops a guinea pig model to characterize the topography of the RWM with high resolution and accuracy and to gain further insight into the optimal geometry of a RWM driver.

Experimental Methods

White light interferometry is a non-contact optical method which measures the micron- to centimeter-sized surface topography of three-dimensional (3-D) structures with sub-micron spatial resolution. The Fizeau interferometery is the basic operating principle and modern peripheral technologies, such as phase shifting, enable fast, precise and economical measurement of a 3-D topographical surface. Briefly, coherent light is separated via a splitter, with one beam directed to the surface of interest and the other to a reflective optical flat. Upon recombining the two beams, interference fringes appear due to the phase mismatch caused by the difference in the optical path length. Two adjacent interference fringes are separated by a phase difference introduced by a change in surface height of 114 wavelength. However, phase shifting technology significantly enhances the out-of-plane resolution up to $1/1000$ wavelength. Thus, upon scanning a 3-D structure, the interference fringes will be recorded as isoheight lines that constitute a topographical contour map. The accuracy of the height and scan speed depends on the qualities of the optics, stage control, and computer processing. A similar technique, such as laser Doppler vibrometry, cannot measure the complete topography of the RWM with large enough scan height.

The present disclosure employed this interferometry technology to measure the topographical profile of guinea pig RWMs. In addition, the geometry of the cochlear bone was measured via micro computed tomography ($\mu$CT). Thereafter, the interferometric RWM measurements were numerically "stitched" measurements with the $\mu$CT cochlea measurements to relate the RWM and cochlear bone. The results were then analyzed in the context of RWM drivers.

1. EXAMPLES

1. Preparation of the Guinea Pig Cochlea Samples.

Carcasses of mature guinea pigs with no history of middle ear disease were provided and euthanized under pentobarbital anesthesia to harvest their tracheas. Within 30 minutes after euthanization, the inner ears were immersed in saline solution by opening the bulla to minimize the coagulation of blood on the RWMs. The inner ears were trimmed by drilling to remove the bone over the RWMs and to ensure the largest possible solid angle view of the RWMs. Consequently, the bones of the vestibular system and oval window were removed.

Inner ears were immediately fixed in 10% neutral buffered formaldehyde solution overnight. Tissues were washed in flowing water and dehydrated with rising concentrations of ethanol (50%, 70%, 80%, 90%, and 100%). After dehydration, the specimens were placed in 50/50 ethanol/hexamethyldisilazane (HMDS) solution followed by 100% HMDS solution for critical point drying to reduce surface tension on the RWMs during the removal of liquid. The tissues were fixed with 2-hour epoxy on a thin silicon plate and cured overnight. The tissues were sputter-coated with gold using Cressington 108 auto sputter coater (Cressington, UK) from three different angles to ensure full coverage of gold on the RWMs.

2. White Light Interferometry.

The topography of the RWM and bone of the cochlea were obtained with 3-D optical surface profilers, NewView 7400 (Zygo, CT). Using Mirau objective lenses, the lateral spatial resolution ranged from 0.56 to 2.83 μm. The fields of view (FOV) were from 1.81×1.36 mm down to 0.36×0.27 mm. Because the typical RWM size is approximately 1.2× 0.8 mm, one scan with the lowest magnification is sufficient to capture the whole view. However, lower magnification tends to leave blank regions in the topographical data. This was mostly ameliorated by the presence of the 10-nm-thick gold layer that improved the efficacy of the reflectance. But, the reflection from the surface of the samples was not strong enough to be clearly distinguished from the pre-scan background, which resulted in blank regions. Furthermore, the scan height of the cochlea and highly-undulated surfaces of the samples made it impossible to optimize the light level for the largest FOV lens. Therefore, by increasing the magnification of the objective lenses and optimizing the light level, preparatory scans were performed to fill in as much of the blank regions as possible. In addition, the cochlea was tilted at 30, 45, and 60 degrees, depending on the samples, to obtain the best angle to capture 1) the flat profile and 2) the recess profile. The speed and maximum length of one scan was 4.8 m/s and 2 mm, respectively, resulting in a duration of 416 s.

The multiple topographical datasets measured with higher resolution were stitched together numerically using MAT-LAB (Mathworks, MA) or built in software MetroPro® (Zygo, CT). When stitching with MATLAB, the multiple topographical data were aligned based on the x-y-z coordinates of the 3-D stage of the Zygo as a reference; the spatial resolution of the 3-D stage was 0.1 µm. The two neighboring scans were measured to share 50% of the area for alignment optimization. Proper alignment was confirmed by calculating deviations along the Z-axis in the overlapping area and performing least squares method with deviation minimization. The recessed region of a RWM was prone to fail in correcting data points because, physically, there is a ledge that obscures the RWM or the light reflection was not sufficient. To scan such a recessed region, multiple scans must be performed from multiple angles. Stitching the multiple scan datasets with multiple angles required a second level of stitching that rotated one surface topography dataset to compensate for the adjusted angle using MAT-LAB. In this second stitching, µCT data were used as a reference to stitch multiple datasets for the complete topography of the RWM surface.

3. Micro Computed Tomography.

X-ray microtomography was subsequently performed to scan the cochlea samples with a µCT scanner (µCT 40, Scanco Medical AG, Switzerland) at an X-ray source voltage of 55 kVp and a spatial resolution of 15 µm. The data were extracted in DICOM format for further processing with MATLAB, including visualization. Each voxel datum contains the absorption intensity of the X-ray scaled with linear attenuation coefficient. To define the bone surface clearly, all absorption intensity voxel data were analyzed with a frequency distribution to determine a "surface value," which defines the boundaries between the bone and the other soft tissues or air; when a voxel has a greater value than the surface value, the voxel is bone. The voxels with approximately a surface value of $1.3 \times 10^4$ cm$^{-1}$ were defined as the surface, and the plane that consisted of these voxels was visualized as the microstructure of the samples.

4. Stitching.

The second stitching of the Zygo and µCT data was performed using MATLAB. The visualized two sets of data were first aligned roughly manually. Because the surface shapes of the bone in the Zygo data and in the µCT data were identical, the multiple sets of Zygo data were snugly "stitched" onto the µCT data at the resolution of the µCT. When a Zygo surface data were aligned manually with the µCT data, a point in the Zygo surface data can coincide with either: 1) the outside, 2) the surface, or 3) the inside of the bone in the µCT data. In this least squares method, the "surface misfit" of the two surfaces was defined numerically such that the surface misfit reaches minimum when the two surfaces are aligned completely. To obtain a quantitative indication of whether the point was on the surface or not, a misfit of each point on the Zygo surface was defined as the squared deviation between the absorption value in the µCT data and the surface value. The summation of all the misfits at each point becomes the numerical surface misfit, i.e., a standard objective function. Using this surface misfit, the Zygo surface was moved and rotated iteratively in 3-D space until the surface misfit was minimized. Multiple Zygo surface datasets were stitched on the µCT bone surface.

5. Curvature Radii of RWM.

The surface shape of the RWM, i.e., the concave and convex structure, has a saddle point at which negative and positive curvatures are shown in different directions. The two curvatures at each point in the Zygo data were expressed as the principal curvatures: the minimum and maximum curvatures of one point on the surface. MATLAB was used to calculate the mean, the two principal curvatures, the difference between the two curvatures, and the two principal directions. The mathematical description follows: 1) the first and second derivatives of the RWM surface and the first and second fundamental coefficients of the surface were calculated; 2) the eigenvectors of the shape operator at each point give the directions of the maximum and minimum curvatures (the principal directions); 3) the eigenvalues correspond to the principal curvatures; 4) the shape operator was calculated using the Weingarten equations.

Results.

Figure 15A:
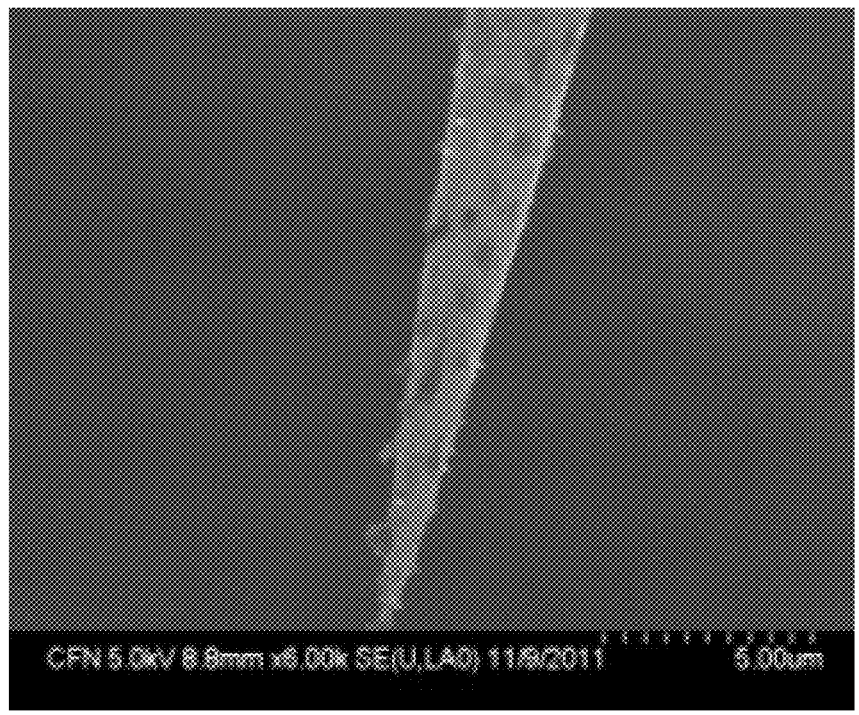
FIG. 15a-b depicts exemplary embodiments of a tungsten indentation probe in accordance with the disclosed subject matter.
Figure 15B:
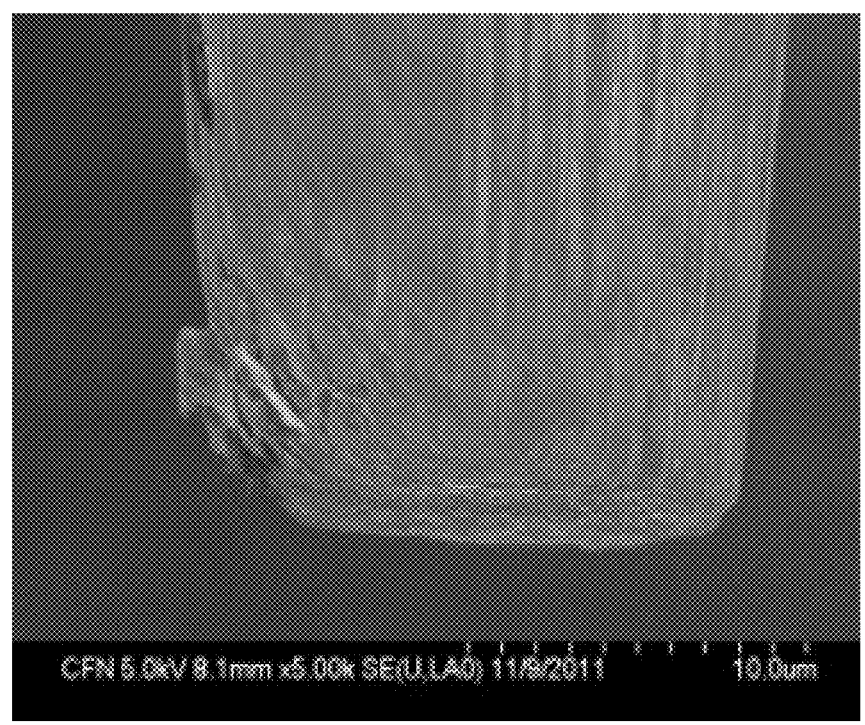

FIG. 9 (a) to (e) show one of the reconstructed microstructures of the inner ear bone scanned via µCT. FIG. 9(a) shows the terminal of the scala tympani indicated at "X" and the exposed basal part of the scala vestibuli. FIG. 15(b) shows the magnified bony terminal limit of the scala tympani. Important landmarks of the terminal are: 1) the most terminal end of the scala and 2) the opposite end of the rim, which is the medial limit and close to the cochlear aqueduct, as shown in FIGS. 9c-e, respectively. The scala tympani extends its spiral canal in the direction of the ledge. At the terminal of the scala tympani, the RWM attachment or RW sulcus, consisting of two layers of bony rims, was found (FIG. 9(c-e)). The outer rim is the terminal of the scala, and the inner rim holds the RWM. The outer rim spirals up from the cochlear aqueduct, making a 360° turn to the same side as the end of the spiral. The inner rim makes a horseshoe shape. Both ends of the rim disappear under the ledge (FIGS. 9(c and e)).

One of the constraints on the design of a RWM driver is the size of the outer and inner rims of the bone. To avoid unnecessary contact between the driver and the bone, a boundary limit was defined by approximating the shape of the bony terminal as an ellipse from the top view. Between the two landmarks defined above, more specifically one point on the inner rim at 1) and one point on the outer rim at 2), lay the longest path, which was defined as the major axis of the ellipse. The minor axis was defined as the longest line segment between two points on the inner rims and the segment perpendicular to the major axis. Among eight samples, the average lengths of the major and minor axes were 1.29 and 0.95 mm, respectively, with respective standard deviations of 11.19 and 12.75%.

FIG. 10 shows three sets of Zygo data of the same sample scanned from multiple angles, aligned, and visualized from one identical perspective. Scanning from multiple angles proved to be an effective way to accomplish complete topography mapping. With an objective lens with a lateral resolution of 1.41 µm, most of the topography of the RWM could be scanned with one vertical scan without leaving blank data points. Lenses with higher magnification were useful in defining the topography with higher precision, but they did not reduce the blank data points significantly. The FOV of 0.95×0.68 mm was not large enough to capture the RWM topography with one scan. Therefore, typically, 3×4 vertical scans and first-level stitching were performed. The total duration for one set of scans for one angle, including preparatory scans, was about two hours. Therefore, three sets of scans required a total of about six hours.

FIG. 11 shows the stitched topographical data obtained by combining the CT and Zygo scans. Two scans from two different angles were sufficient to obtain almost full coverage of the RWM surface. The top-view scan (FIG. 10, left) showed a gap in the scatter plot data that corresponds to the RW sulcus and to the recess under the ledge. In the stitched data (FIG. 11, left), it was clear that the gap was the surface of the bone structure, not RWM, and the top-view scan was found to be an effective method for acquiring the most area of a RWM. The topography of this gap was scanned with one, 45°-angled scan (FIGS. 10 and 11, middle). Most of the portion of the RWM surface hidden under the ledge was scanned by the other, 45°-tilted scan (FIGS. 10 and 11, left and FIG. 12). However, an area remained for which there were sparse data points, i.e., the deepest and most highly-angled portion of the RWM that partly precluded both gold sputtering and direct optical observation. Anatomically, this area is connected to the round window membrane pouch-like extension (RWME) and as well as to the cochlear aqueduct.

FIG. 13 shows the surface curvatures of the RWM surface (shown in FIG. 12, middle) at approximately the same angle, but excluding the surface of the bone. Only the top-view scan data were used to calculate the curvatures to consider the implications for the RWM driver, because the driver cannot access the surface under the ledge. Positive and negative curvatures correspond to convex and concave surfaces, respectively. FIG. 13(a) shows the mean curvature of the RWM surface, indicating a relatively large area of flat surface, with the average ranging from $-0.5$ to $1.7$ mm$^{-1}$. The area shown with a dashed line rectangle was used to calculate the means and standard deviations for the four types of values across the RWM. The mean curvature was $-0.21$ mm$^{-1}$ with a standard deviation of mean curvature of $0.098$ mm$^{-1}$. The curvatures become highly variable in the area close to the RWME. FIG. 13(b) shows the maximum curvature at each point. The flat area shows variation of the curvature in stripes ranging from 0 to 3.1 mm$^{-1}$. The mean was $0.71$ mm$^{-1}$ with a standard deviation of $0.13$ mm$^1$. The stripe pattern was parallel to the minor axis of the RWM. In FIG. 13(c), the minimum curvature contour plot shows a similar stripe pattern parallel to the major axis of the RWM. The variation ranges from 0 to $-1.9$ mm$^{-1}$. The mean was $-1.13$ mm$^{-1}$ with a standard deviation of $0.14$ mm$^{-1}$. FIG. 13d shows the difference between the maximum and minimum curvatures at each point. The mean was $-1.84$ mm$^{-1}$ with a standard deviation of $0.18$ mm$^{-1}$.

According to the findings, the preferred embodiment of the driver: 1) avoids collision with the bone and prevents damage to the bone structure. In embodiments where a transducer or optical microscope is included, the preferred driver: 2) maximizes the energy transfer efficacy to the perilymph fluid; and 3) minimizes the stress within the RWM to minimize the possibility of rupturing the RWM due to repetitive extension and contraction of the membrane.

For the first requirement, the major and minor lengths of the bony terminal μCT scan provided useful information for the size restriction of the transducer. In general, the second and third requirements are in a trade-off relationship. The vibration energy of the transducer is transferred by the displacement of the membrane from the initial state. The displacement of the membrane, in turn, causes the strain and stress on the membrane. Under this consideration, a point loading on the center of the membrane with vertical oscillation is the most effective way to maximize the magnitude of the displacement, but at the cost of concentrating the stress. An osculating sphere that maximizes the contact area between the RWM driver and RWM surface effectively minimizes any stress concentration. Because the RWM topography has a saddle point, one approach based on the data for the design of the RWM driver is an osculating sphere with the radius of the sphere equal to the curvature radius of the RWM along the minor axis. When such a sphere makes a contact with the RWM, the surface area in contact is minimized in the major axis direction and maximized in the minor because of the convex and concave curvatures. Thus, an osculating sphere in the minor axis serves as an initial point in the design because it considers both the efficacy of energy transfer and the concentration of stress.

Finite element modeling (FEM) is a powerful method for studying the energy transfer, stress, and strain caused by the displacement of the RWM using myriad designs of transducers and couplings onto the RWMs. The detailed RWM topography data measured in the present disclosure establish the foundation for FEM studies. Another variable, such as thickness, is indispensable in mechanical modeling as was previously determined via histological studies. The RWM thickness of rodents is known to be uniform and a single cell-layer structure. Reconstructions of the 3-D structure of guinea pig RWMs using orthogonal-plane fluorescence optical sectioning microscopy show that the RWME was the only place that had a multi-cell layer.

Fixation and dehydration force the RWM specimen to undergo significant biochemical changes. This poses a question as to the extent of the effects of fixation on the stress and strain in the RWM. The physiological condition of the RWM must be maintained during the topography mapping to better understand the physics of the interaction between the transducer and a RWM. In some embodiments, zinc oxide nanoparticles can be employed to improve the reflectance of the transparent surface of the RWM with minimal biochemical reaction with the soft tissues. The duration of a set of vertical scans in the present disclosure indicate that the measurement the surface topography of the RWM in vitro simulating physiologic conditions can be performed. Furthermore, by controlling the pressure within scala tympani from scala vestibuli, it is possible to analyze the relationship between scala tympani pressure and RWM topography in the detail demonstrated in the present disclosure.

The present disclosure also demonstrates that a white light laser scanner is a powerful tool for measuring the complete surface topography of the RWMs of guinea pigs with submicron resolution. A customized software, "stitching" was developed to combine multiple scans to capture the entire topography of the terminal of the scala tympani. Furthermore, μCT is a complementary technology that allows imaging of the soft tissue, clearly distinguishing it from the bone. The curvatures of the surface of the RWM were analyzed and found to show a saddle point, and strip patterns perpendicular to both major and minor axes of the elliptical shape of the RWM.

Figure 41:
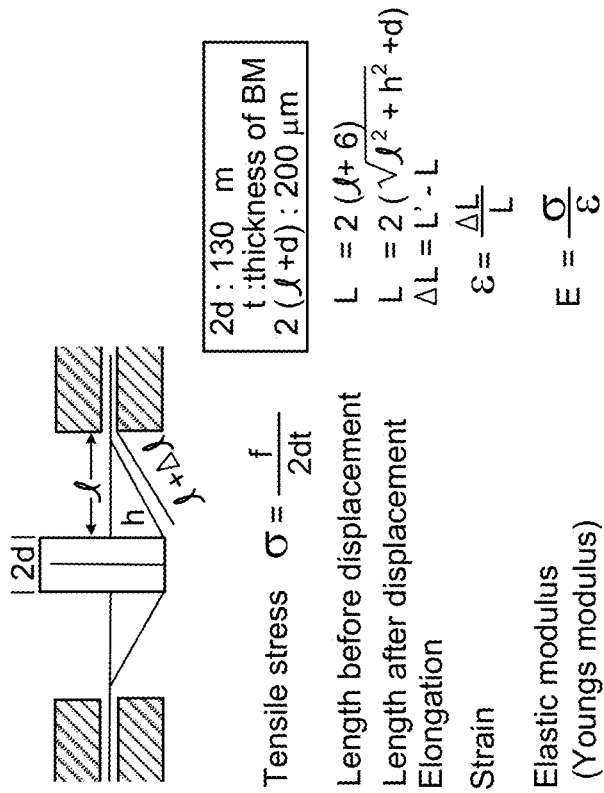
FIG. 41 shows Table 2 representing the elastic moduli of human round window, basilar and Reissener's membranes of subjects and the deformation below an indentor.

A preferred micro-needle array has an adequate safety margin to avoid failure while penetrating the RWM. The primary cause of a failure is buckling of needles. The safety margin is defined as the ratio of the force that that causes buckling of the needle array to the force required to penetrate the RWM. To estimate the safety margin by a simulation of the RWM penetration by the micro-needle array, the mechanical properties of the RWM (i.e. Young's modulus and tensile strength) need to be determined. Previous analyses of the mechanical property of human RWM are not truly reflective of the mechanical property of the RWM as they do not have the proper physical model to analyze the experimental data: the model simplified the deformation as a homogeneous elongation of the membrane and neglected the stress concentration induced by the bending of the membrane. Further, as seen by the excerpt in FIG. 41, Table 2, the deformation of the membrane below the indenter was neglected even though the relative dimension of the needle was quite large.

Figure 14:
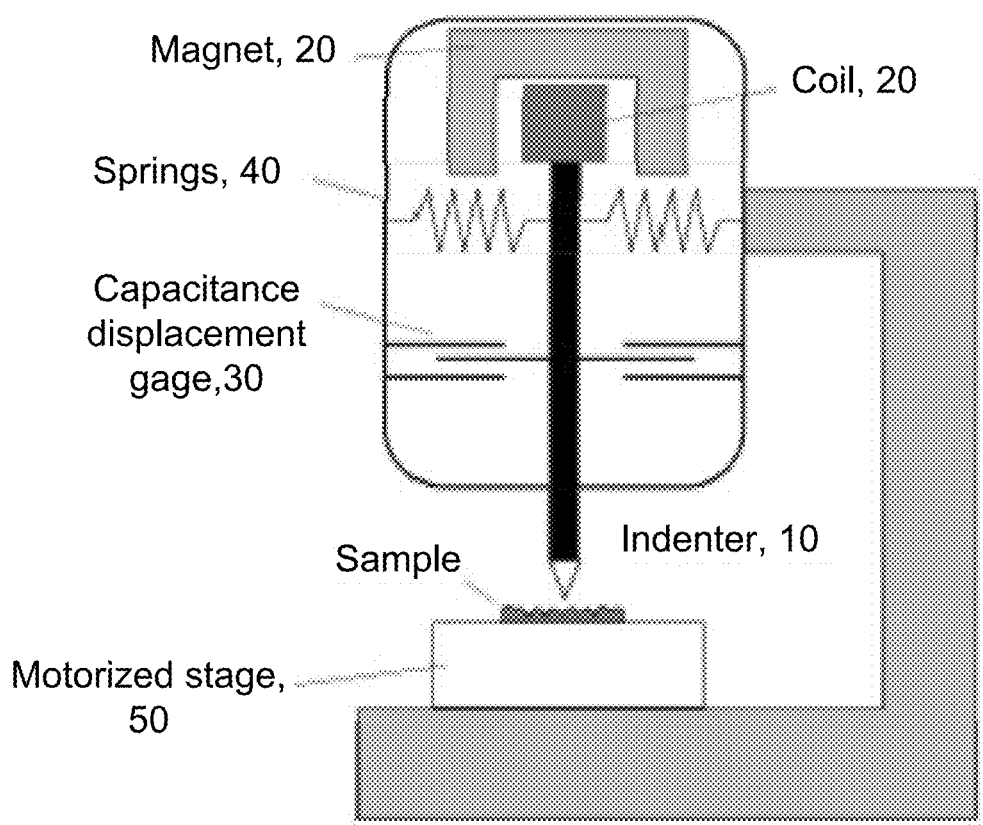
FIG. 14 is a schematic representation of nanoindentation of a sample membrane in accordance with the disclosed subject matter.

The limitations of the prior study were overcome in the present disclosure by the use of a nanoindenter. A schematic representation of a nanoindenter is shown in FIG. 14. The main shaft (10) of the nanoindenter is mounted in linear bearings so as to allow motion of the shaft along its axis, which is effected by a set of magnetic coils (20). Thus the position of the shaft is determined and controlled by the electric current flowing through the magnetic coils. The position of the nanoindenter shaft is measured using an electrical capacitance gauge (30). A set of leaf springs (40) of known stiffness deforms when the shaft moves; the force exerted onto the nanoindenter shaft can then be determined from the known deflection and stiffness of the springs. A motorized stage 50 is provided which can move in the x and y-direction to allow for multiple operations of the nanoindentor to form a series of holes in the sample. An indenter tip, of a very hard material, is mounted on the shaft. Typical nanoindenter tips are made of diamond, however tungsten wires can also be employed which are micro-machined to different tip shapes and sizes, as seen in FIGS. 15a-b. Although two exemplary embodiments are shown for purpose of illustration and not limitation, it will be understood by artisans of ordinary skill that alternative geometries can be provided, as so desired. Sophisticated feedback control systems can then be used to prescribe either the displacement or the force on the indenter shaft as a function of time.

In one embodiment, the nanoindenter tip is indented into a material. The force and the displacement on the nanoindenter tip are measured during this process. In some embodiments, the material will be a free-standing RWM membrane or a proxy material. The membrane itself deflects globally even as the sharp tip indents locally into the deforming material. Hence, the total measured displacement is the sum of the local and global displacements. From the measured force-displacement data, various material models can be employed to determine the mechanical properties of the suspended membrane. An example of a force-displacement curve related to indentation into a RWM is in FIG. 16a-b. For an ideal linear-elastic membrane, the force increases as the cube of displacement; this behavior can be seen approximately in FIG. 16b at the earliest stages of indentation. Then at an indentation depth of about 75 micrometers, the character of the force-displacement curve changes abruptly. This is a signal that the indenter tip has begun to penetrate the membrane locally rather than only to deflect globally the membrane. The post-penetration behavior of the force-displacement response depends upon the details of the shape of the indenter tip, and is one of the degrees of freedom employed in accordance with the disclosed subject matter.

One of the main requirements for accurate analysis of the force-displacement response of an indented material is to determine accurately the indenter position at which the tip first comes into contact with the membrane. Traditional methods to determine the point of contact rely on measurement of a non-zero force, but the potential for significant error identifying contact exists due to many different experimental factors. To that end, a dynamic method is employed to determine the point of contact. A linearly varying displacement of the nanoindenter tip with respect to time as it approaches the surface is prescribed, and superimposed thereupon is the linear motion a sinusoidal variation of displacement with respect to time with amplitude of a few nanometers. The phase lag between the prescribed position and the measured force on the indenter tip is then monitored. The nanoindenter system is sufficiently sensitive to be able to measure the drag force of the nanoindenter tip as it moves through air. Thus, the force lags the displacement slightly even in air. However when the nanoindenter tip comes into contact with the surface of the material of interest, there is a sudden increase in the phase lag over the distance of just a few nanometers of displacement. With this method it is possible to obtain repeatedly a significantly greater precision of the contact position.

For example, the nanoindenter can be the Agilent G-200. The Agilent G-200 nanoindenter includes a Nanovision option for contact imaging, a Lateral Force Measurement module, a High Load Option, an XP indenter head (force resolution of 50 mN, maximum force of 500 mN, displacement resolution of 0.01 nm, maximum indentation depth 500 µm) with Continuous Stiffness Monitoring capability, Dynamic Contact Module (DCM) indenter head (force resolution 1 mN, maximum force 10 mN, atomic scale displacement resolution, maximum indentation depth of 15 µm) with Continuous Stiffness Monitoring capability, and TestWorks 4 Explorer Level software package to control the system and to record the output. The mounting fixture for the nanoindenter tips is versatile and robust, which is compatible with the wide range of different nanoindenter tips (both in shape as well as surface roughness) which can be employed in accordance with the present disclosure. Exemplary experiments have used custom-made tungsten tips shown in FIG. 15a-b. The high Young's modulus of the tungsten (i.e. 411 GPa) makes it possible to ignore the deformation within the nanoindenter tip as there is little to no contribution of the tip deformation to the measurement. However the deformation within the tip is not negligible for the silicon array of micro-needles employed in accordance with the disclosed subject matter, which requires extensive modeling to ensure the indenter tip acts as intended.

The disclosed subject matter will present numerous advantages over conventional inner ear treatment devices and methods, and will provide numerous benefits to patients. For purpose of illustration, and not limitation, some specific aims of the presently disclosed subject matter are set forth below.

Aim 1. Characterization of Mechanical Properties of the RWM Using the Nanoindenter.

Rational:

Without biophysical modeling of the interaction between the RWM and micro-needle array, the design of the micro-needle and its penetration of the RWM is heuristic rather than reductive. Nanoindentation is a robust experimental tool to effect micro-needle penetration of RWM. The reliability of the micro-needle array is quantified as a factor of safety (FS) that is defined by the ratio of the load that causes the failure of a micro-needle divided by the force that is required to penetrate the RWM. In accordance with the disclosed subject matter, the indentation load and displacement at rupture of the RWM is measured. The Young's modulus and strength at perforation is estimated using the ABAQUS finite element modeling (FEM) by comparing the simulated force and the deflection required for a micro-needle array to cause rupture of the membrane to the experiments.

Methods:

Two tungsten probes, one with tip curvature of 0.4 µm and the other a 20 µm flat probe, are employed initially in nanoindentation (FIG. 15a-b). A Guinea pig cochlea is extracted and kept in a cold saline solution until placed in the nanoindentation chamber. The cochlea is placed in the chamber with the RWM facing upward. The contact of the tip on the RWM is confirmed either manually when the load rate steadily exceeded 0 N/m with an indentation speed of 1 µm/sec, or via the phase lag method. The completion of the rupture is determined by the characteristic behavior of the force-displacement curve. The rupture diameter is confirmed visually with a 10× microscope objective mounted on the nanoindenter.

Figures 16A, 16B:
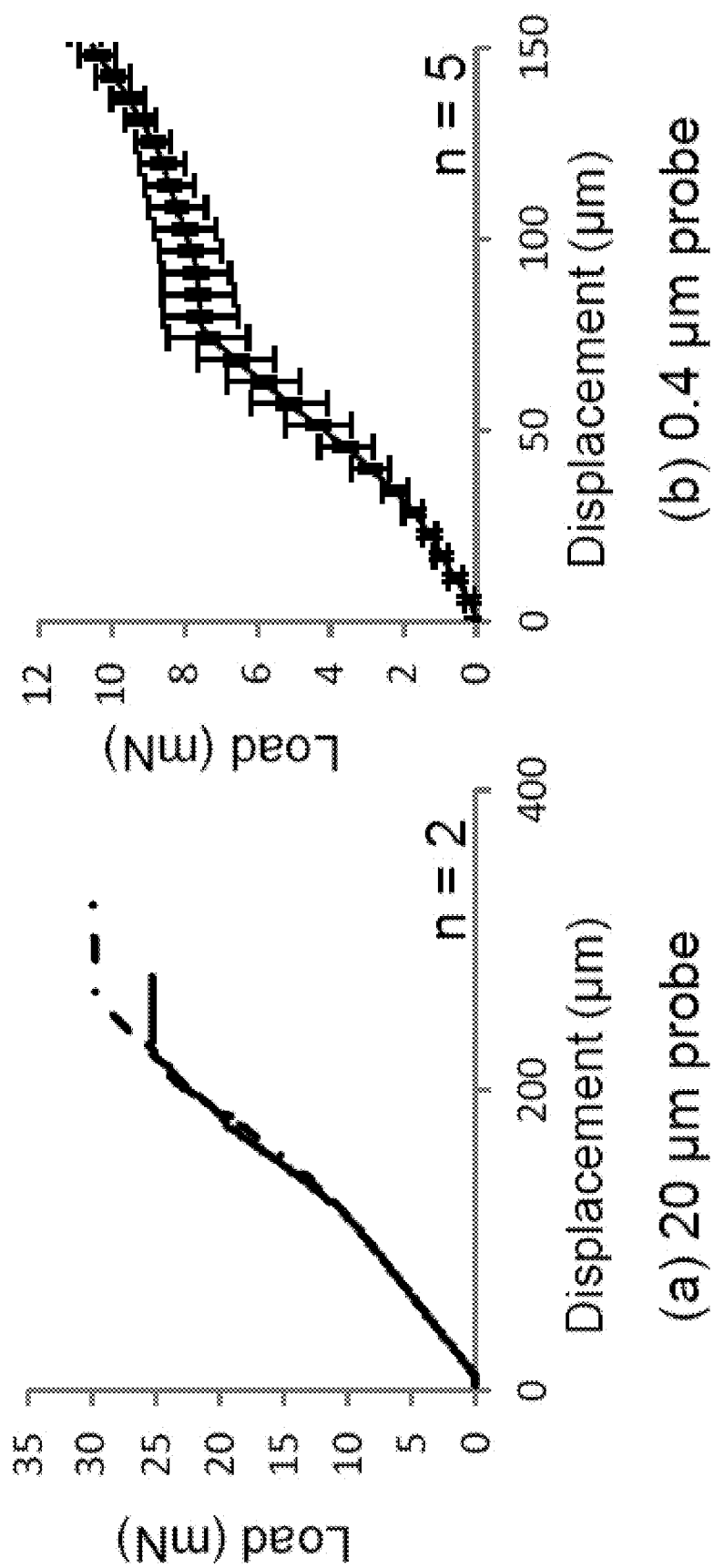
FIG. 16a-b depict graphical results of a load displacement curve.

The results obtained with these methods are shown in FIG. 16a-b. The force-displacement curve obtained with 20 µm probe shows more than 20 mN load and 200 µm displacement (FIG. 16a) at the time of penetration. The diameter of the rupture was about 20 to 50 µmin diameter. The 0.4 µm tip penetrated the RWM at less than a 10 mN load and 80 µm displacement (FIG. 16b). The indentation was stopped after the indenter traveled an addition 100 µm through the perforated RWM to ensure a visually detectable perforation. The resulting hole of less than 10 µm diameter was visible under the microscope.

To estimate the Young's modulus and strength at perforation, the rupture process will be modeled numerically using ABAQUS. For a guinea pig, the RWM rupture is modeled as being axisymmetric with a 1.2 mm diameter and a 10 µm thickness assuming, initially, an isotropic, linear-elastic material; other material models such as hyperelastic models, is implemented as necessary. The model employs pinned boundary conditions along the rim and indenter is modeled, initially, as a rigid body of the shape of the indenter tip that displaces the RWM; the elastic properties of the indenter tip is taken into account as necessary. The relevant mechanical properties (e.g. Young's modulus) is determined by fitting the simulated force-displacement results to the experimental data. The strength at perforation is estimated from the maximum von Mises stress—which is an invariant measure of the stress.

Figure 17:
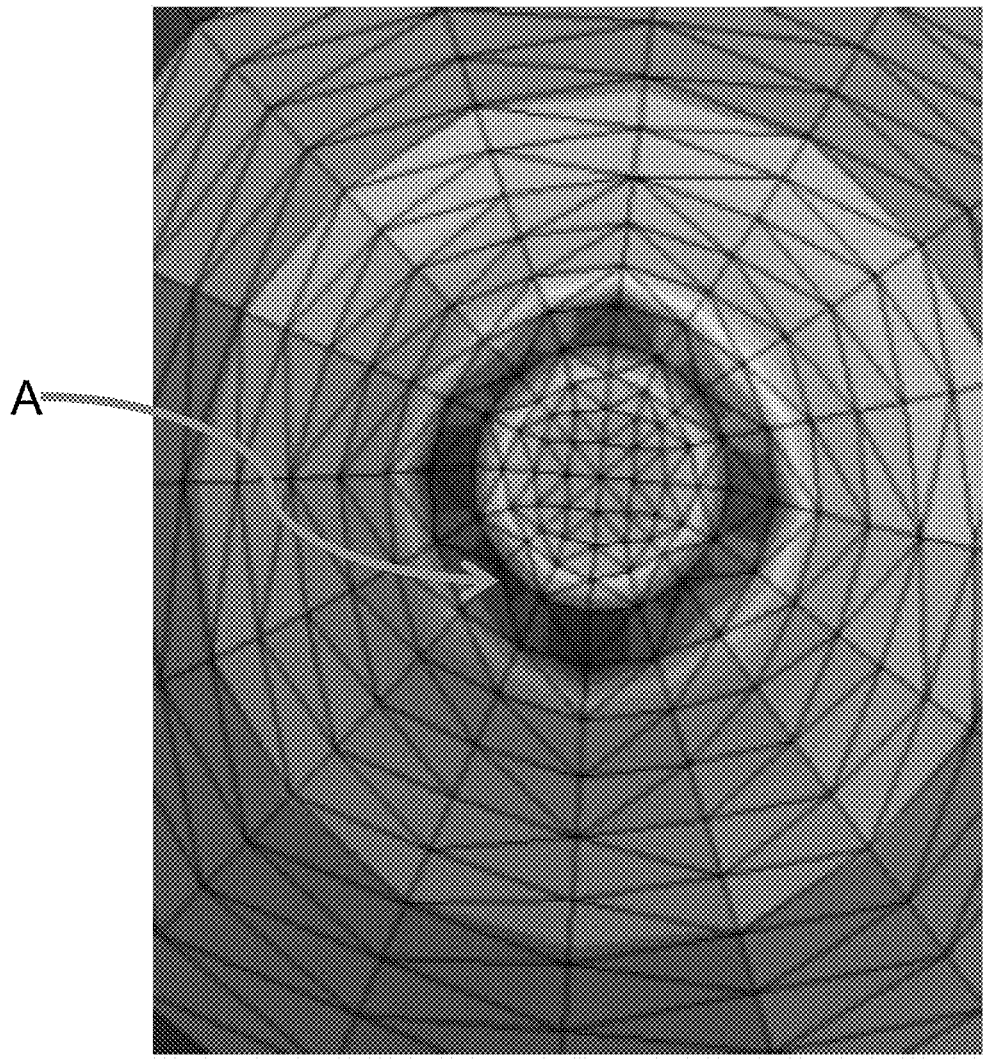
FIG. 17 depicts graphical results of an indent stress plot.
Figure 18:
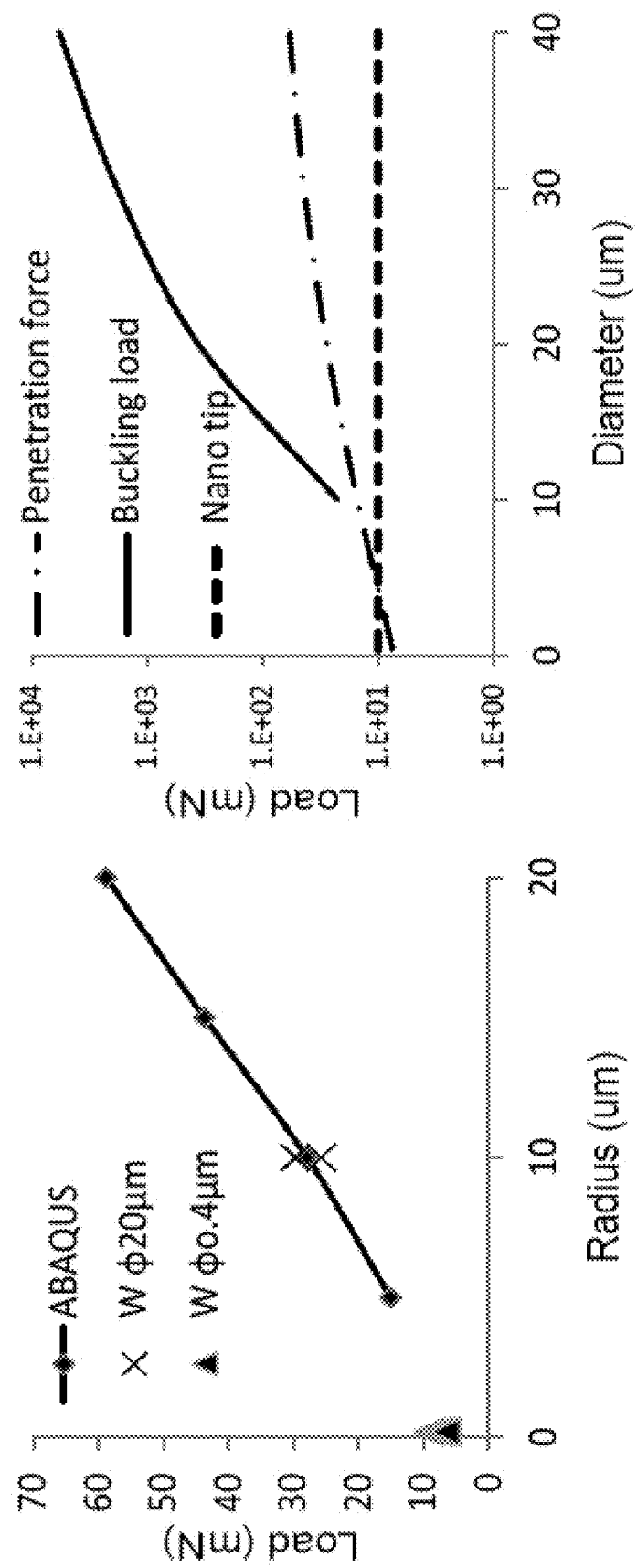
FIG. 18 depicts graphical results of a load decrease by probe radius plot and a safety margin estimate.

Based upon preliminary studies, the Young's modulus was estimated to be about 100 MPa, which is quite high, but this can indicate a high collagen density in the RWM. The calculated Von Mises stress in the RWM under the indenter is shown in FIG. 17; the high stress area (A) indicates that the rupture likely initiated around the edge of the tungsten probe. Results of FIG. 18 shows the force at perforation of a guinea pig RWM for the two tungsten tips in FIG. 15a-b. In addition, preliminary ABAQUS calculations for the force at perforation for a flat indenter as a function of diameter are shown in FIG. 18, assuming perforation occurs at a critical von Mises stress. These results suggest that the load is proportional to the radius of the probe tip.

FIG. 18 shows a reliability estimate of the micro-needles that compares the buckling force of a nanoindenter tip to the force at perforation, the ratio of which is the safety factor, FS. These results suggest that by reducing the tip diameter below 1 µm, the rupture force can be reduced down to 10 mN. Thus, a 10 µm and 20 µm radius needle will have FS of 2 and 36 respectively. In this study, the buckling force is calculated based upon modeling the actual geometry of the indenter tips fabricated and employed in the experiments. The pertinent boundary conditions are to fix one side against displacement and to allow the other end freedom to displace and rotate. Then a buckling analysis is performed to determine when the nano-needles are expected to fail due to lateral motion (either buckling or bending).

Furthermore, the penetration of the membrane with micro-needle array is modeled to estimate the FS due to the two failure modes (i.e., buckling and bending) by calculating the loading force and bending moment on each needle. A preliminary result indicates that the ability to effect rupture of the RWM with the same load on each micro-needle is improved by judicious positioning of the needle on the RWM surface.

Experimental characterization of at least twelve different guinea pig RWMs was performed. One mode of experiment is the perforation experiments. A second mode of experiment is to place the RWM on a flat hard (e.g. silica) surface in a saline solution bath and perform flat punch indentation. One advantage of the second mode is that the experiment can be repeated several times on each RWM without major modification of the mechanical response of the system. Additionally, Student's t-test or ANOVA, as appropriate, can be performed on the results.

Figure 19:
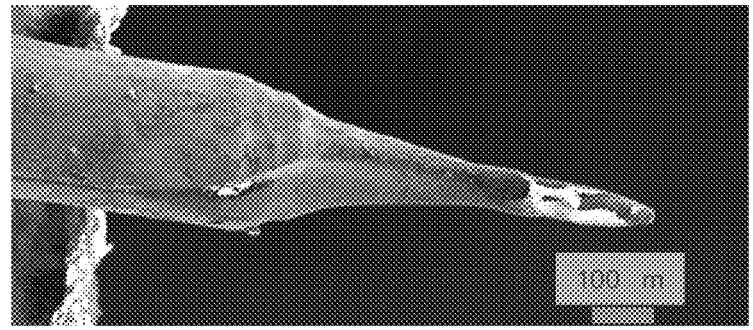
FIGS. 19-20 are an exemplary view of a nanoindentor and corresponding perforations in the RWM made in accordance with the disclosed subject matter.
Figure 20:
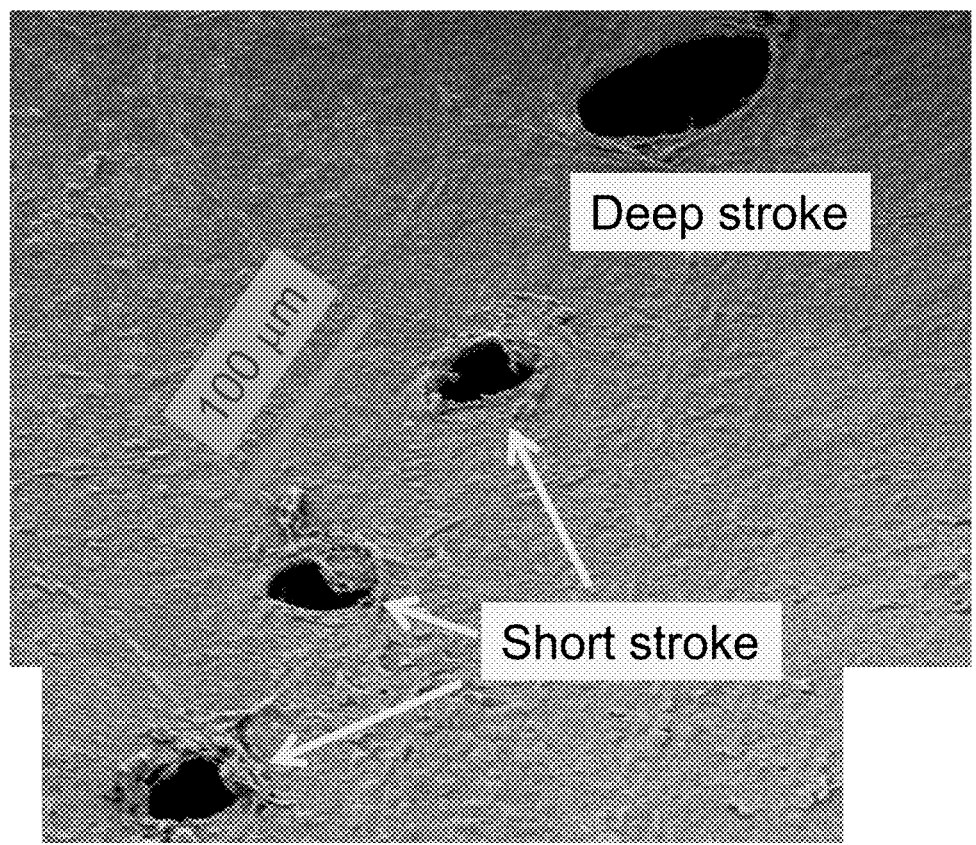

FIG. 19 depicts an exemplary nanoindentor which was configured as a 20 µm tapered needle and employed to form a series of perforations in the RWM, as shown in FIG. 20. As the perforations are disposed closer to each other, the structural integrity of the membrane becomes compromised which can lead to undesired tearing or elongation of the perforation. Accordingly, in the exemplary embodiment shown in FIG. 19, the midpoint of each perforation is spaced approximately 100 µm apart. Additionally, the depth of penetration of the nanoindentor can affect the perforation size. In this regard, FIG. 20 depicts three short stroke perforations and one deep stroke perforation, with the perforations of the short strokes being smaller relative to the deep stroke perforation.

Figure 21:
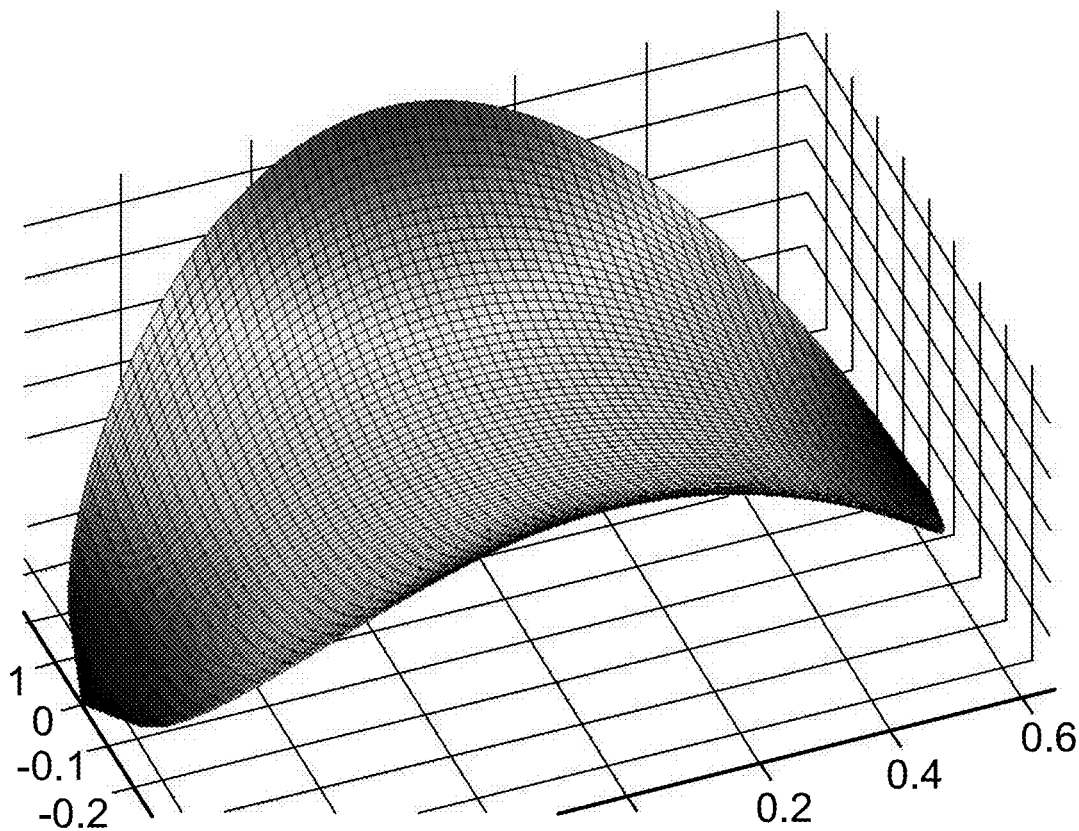
FIGS. 21-22 are an illustration of the saddle point contour of the RWM and the corresponding load vs. displacement plot.
Figure 22:
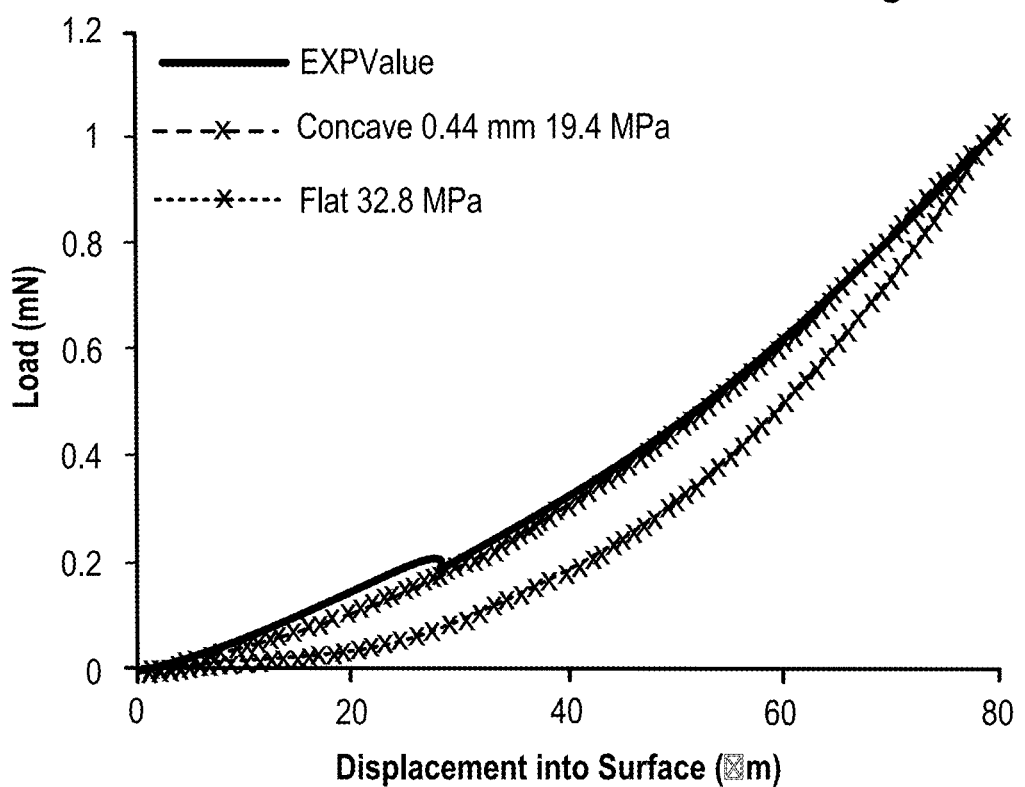

In accordance with another aspect of the disclosure, the mechanical property characterization of the RWM allows for an understanding of the relationship between the load (of the needle or nanoindentor) and the displacement into the surface of the membrane. As previously discussed with regard to the shape and contour of the RWM, the negative and positive curvatures of the RWM represent a saddle point, as shown in FIG. 21. A corresponding graph of the load vs. displacement is provided in FIG. 22 which depicts the expected value (based on a Young's Modulus of 19.4 MPa), as compared to the values at the flat portion of the saddle point and concave portion of the saddle point (i.e. proximate the longitudinal ends on the x-axis).

Figure 23:
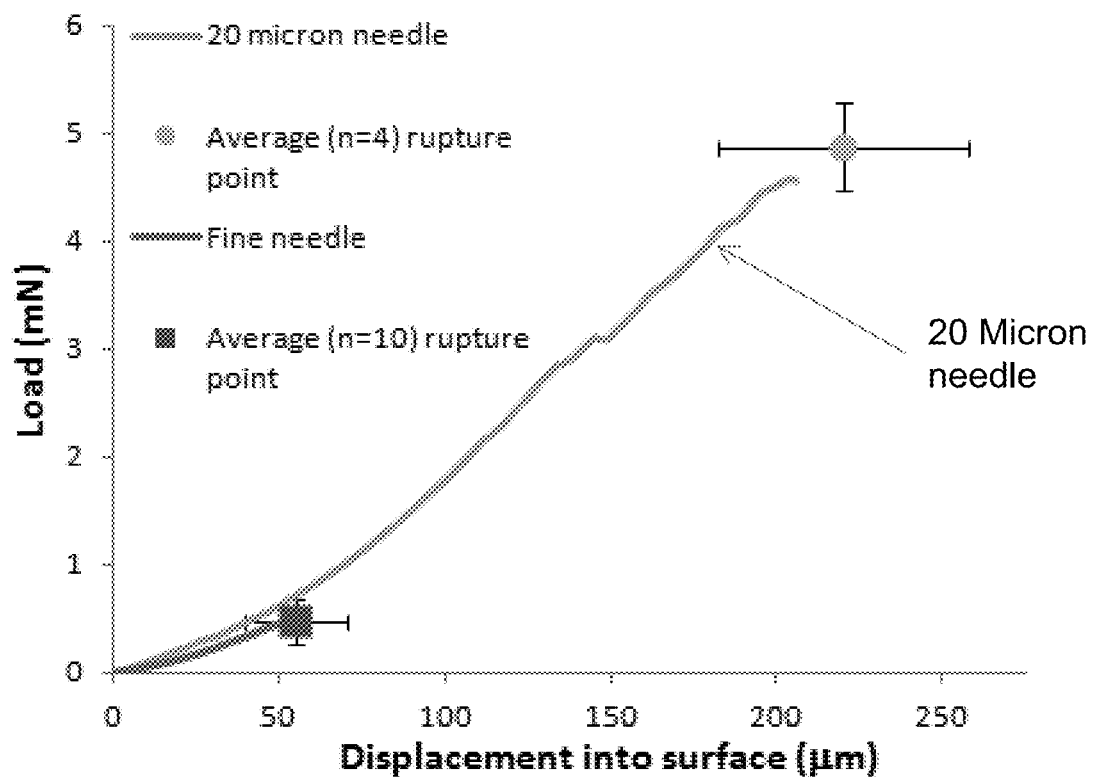
FIGS. 23-24 are an illustration of the load vs. displacement plot and stress plots, respectively.
Figure 24:
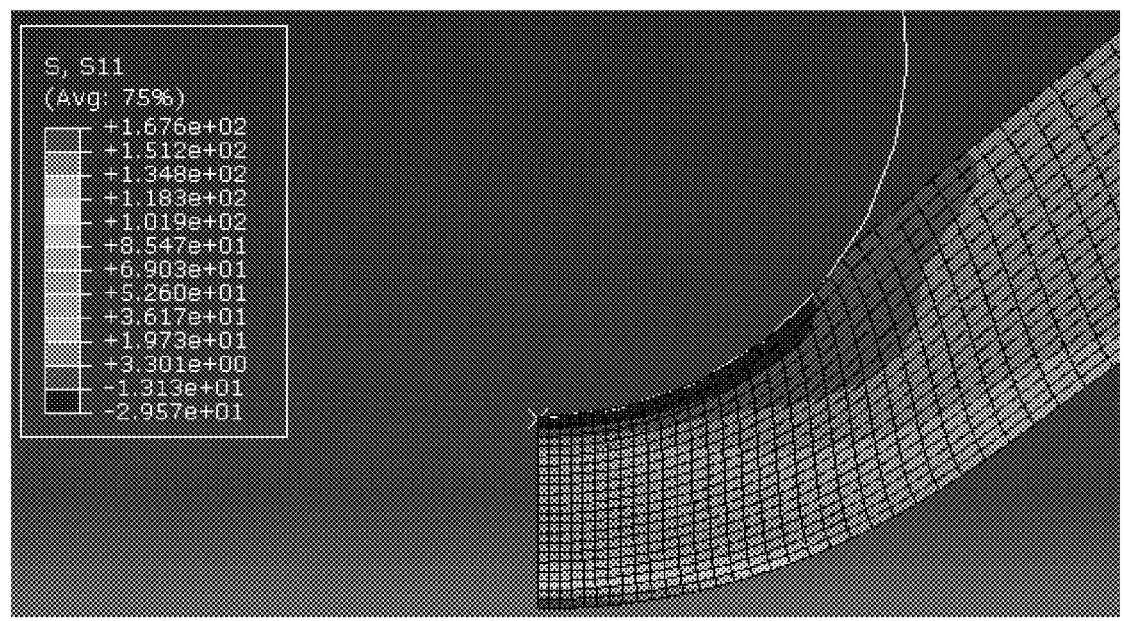

Furthermore, the present disclosure analyzed the load vs. displacement relationship for different size needles. As shown in FIG. 23, the load vs. displacement curve is provided for a 20 micron needle as well as a Fine needle. Additionally, a plot of the stress at the point of rupture is provided in FIG. 24 (based on a Young's Modulus of 170 MPa).

Aim 2. Based on the Mechanical Properties of the RWM, Design Micro-Needles for Creating Microperforations in the RWM.

Design Based on the Nanoindentation Results.

The force and displacement indicate that to produce a 20 µm diameter hole the needle should withstand an axial force of at least 10 mN. Also, a 100 µm length is necessary to ensure the substrate of the micro-needle does not touch the RWM. To maintain a FS of 10 against buckling failure, a 10 µm diameter 100 µm long Si column with tip size of 2 µm is used.

Figure 25:
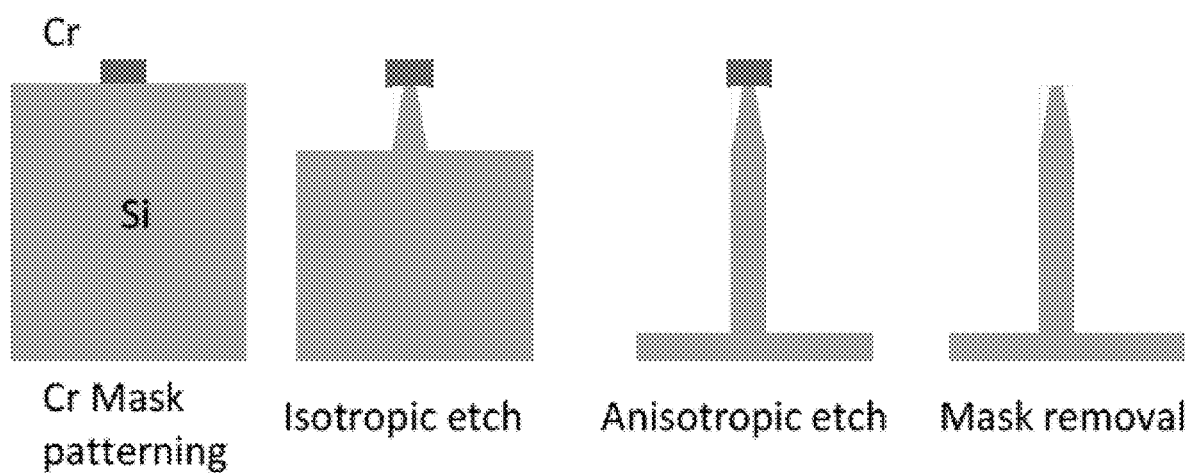
FIG. 25 depicts various stages of fabrication of a micro-needle array in accordance with the disclosed subject matter.

In an exemplary embodiment, the fabrication process of the micro-needles is by isotropic etching combined with cryogenic processes that produce a taper. FIGS. 5 and 7-8 shows a single φ10 µm micro-needle in addition to a 10×10 array of φ20 µm micro-needles. The fabrication parameters are optimized to produce the designed shape based upon fabrication processes shown schematically in FIG. 25. The micro-needles (with 10, 20, 50 µm diameter) are patterned by a Chromium mask on glass with (DWL 2000, Heidelberg instruments) in 2-dimensional arrays. These patterns are transferred to 100 nm chromium thin films of on the Si wafer by optical lithography using a mask aligner (MA/BA6, SUSS MicroTec) followed by physical vapor deposition (PVD75, Kurt J. Lesker) and lift off with solvent (Remover 1165, Microposit). The chromium mask protects the Si from etching to allow formation of the micro-needles. The tip diameter is formed by isotropic Si etching with $SF_6/O_2$ gas in a Reactive Ion Etcher (RIE) (Trion Phantom III). The shaft is created by anisotropic Si etching with cryogenic $SF_6/O_2$ process in a Deep Reactive Ion Etcher (Oxford Plasma Lab). The chromium mask is removed by wet etching. The fabricated silicon wafer is diced to have a 1 mm square stamp with micro-needle array.

Aim 3. Analyze the Different Designs of Micro-Needles and their Ability to Create Micro-Perforations and to Characterize the Size and Nature of these Perforations.

Aim 3.1 Introduction of Micro-Perforation and Reliability Evaluation.

Rational:

The needle array of the present disclosure allows for simultaneous perforations of RWM. The physical interaction of the needle array and RWM can be predicted from the single tungsten needle penetration with some degree of uncertainty. The likelihood of failure of the micro-needles must be clarified in order to optimize the micro-needle array design and the penetration method. The load that causes buckling and bending failure of the micro-needle can be determined. By indenting the fabricated micro-needle on the well-defined hard substrate as well as the RWM in situ, the reliability of the micro-needle array is assured.

Methods:

The reliability of the exemplary micro-needle is tested by the nanoindenter. The micro-needle array is attached to a nanoindenter tip fixture. First, the buckling and bending force is determined for an individual micro-needle by pressing the micro-needle onto a block of fused silica (E=72 GPa, H=9 GPa) and (E=0.5 MPa, H=7.1 MPa). The buckling is characterized by vertical loading and the bending is characterized with the lateral forces.

The fabricated micro-needle array is mounted onto the nanoindentater to penetrate a guinea pig RWM. The specimen and the mechanical interaction characterization are as described above in Aim 1. The micro-needle array is lowered to the membrane and penetration is performed. The diameter of the micro-needle is varied by the fabrication process to obtain an FS of 1. The number of micro-needle in the array varies from 1 to 2×2 to 10×10 to quantify the effects that arise from the geometry and the number of needles. The mode of damage to the micro-needle is confirmed by optical microscope and scanning electron microscope. Buckling or bending are the primary causes of the failure. Numerical models in ABAQUS are optimized to examine the significant mechanical characteristics that lead to failure. At the same time, to develop a method to safely introduce micro-perforations during in vivo experiments, the contact detection criteria and subsequent loading variables until the RWM perforation are determined.

After the first needles in the array penetrate the membrane, friction between the needles and the membrane may serve to reduce the efficacy of the penetration by the remaining needles. The membrane deflection may induce lateral forces on the needle by friction resulting in bending failure of the needle.

Aim 3.2 Micro-Perforation Diameter Determination.

Rational:

The shape of the hole generated by the micro-needles determines the diffusive permeability improvement, the fluid dynamic leakage prevention and the level of damage to the cellular architecture. Thus, control over the hole size by the tuning the needle shape and subsequent required applied force, displacement and indentation rate by the nanoindenter is desirable. Additionally, the inelastic deformation that induces the hole can be characterized.

Methods:

The perforated round window membrane is stained with hematoxylin and eosin after fixation. Using a high numerical aperture lens, the cross section of the hole is scanned vertically. The 3-D structure of the perforation is examined.

The size of the RWM can be different from the micro-needle diameter. For example, a 20 µm tungsten tip causes a bigger hole than the tip diameter. In accordance with an aspect of the disclosed subject matter, an understanding of the inelastic and elastic properties of the RWM in order to determine the underlying deformation mechanisms and control the perforation diameter is provided. Even though there is a significant difference between the mechanical and cellular architectural of the human and guinea pig RWMs, this development system can be applied to the human RWM model smoothly. The micro fabrication batch processing allows several different geometries to be fabricated at a time to accelerate development.

Aim 4. In Vitro Characterization of the Changes in Permeability Associated with Micro-Needles.

Rational:

The permeability improvement of the RWM is quantified in vitro using confocal microscopy. Guinea pig *cochleae* is used as a model system because of the relatively ample number of studies. In vivo experiments impose difficulties to address specifically the diffusive permeability improvement by the micro-perforation. Agar is used to exclude convection and study specifically diffusive transport of molecules. Additionally, a Confocal microscope is employed to quantify the movement of fluorescent molecules via diffusion in the micro-perforation with sub-micron resolution.

Aim 4.1 Macroscopic Permeability Experiment.

To quantify the permeability, the diffusion of fluorescent dyes through the perforated RWM is studied. Rhodamine B is used as a model molecule because its molecular size and diffusion coefficient are close to the two therapeutic reagents.

Aim 4.2 Microscopic Diffusion Study.

To study the diffusion through the micropore in detail, confocal microscopy is performed. The agar diffusion channel is again used. In one embodiment, the focal plane is fixed to include the pores in the plane.

Figure 26:
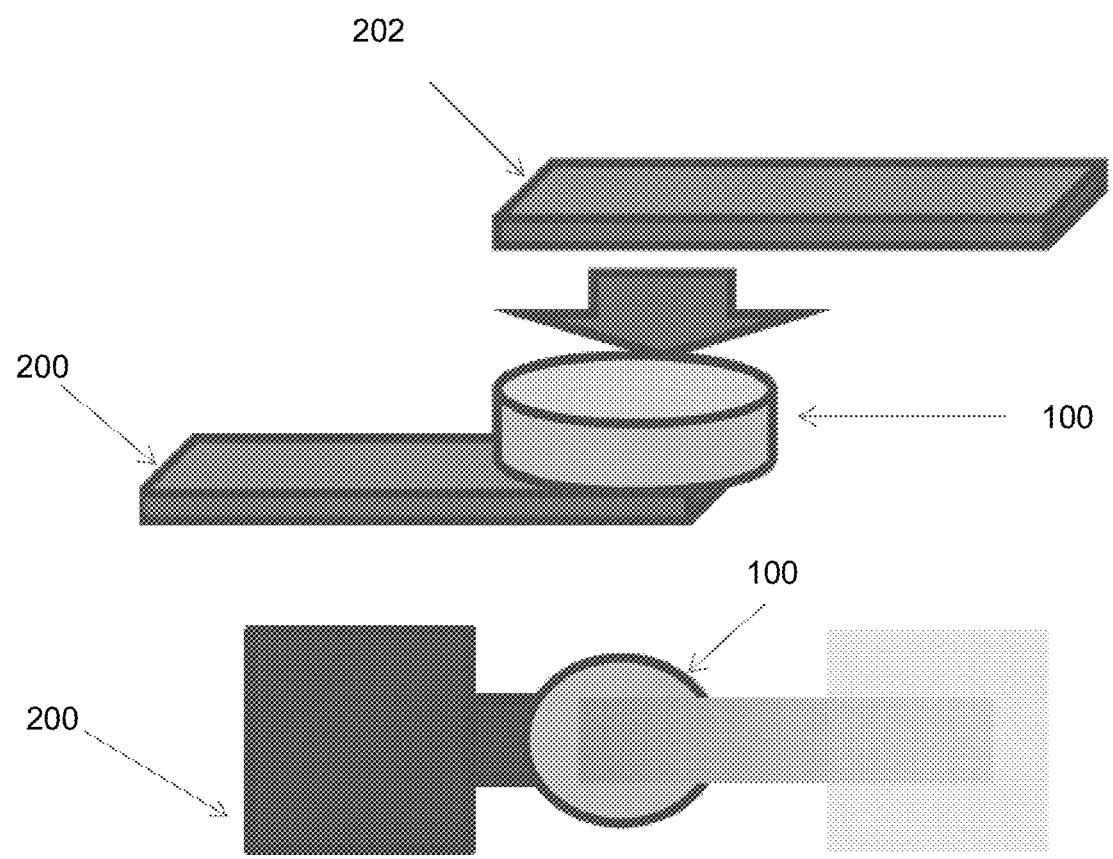
FIGS. 26-27 is a schematic figure of a permeability procedure in accordance with the disclosed subject matter.
Figure 27:
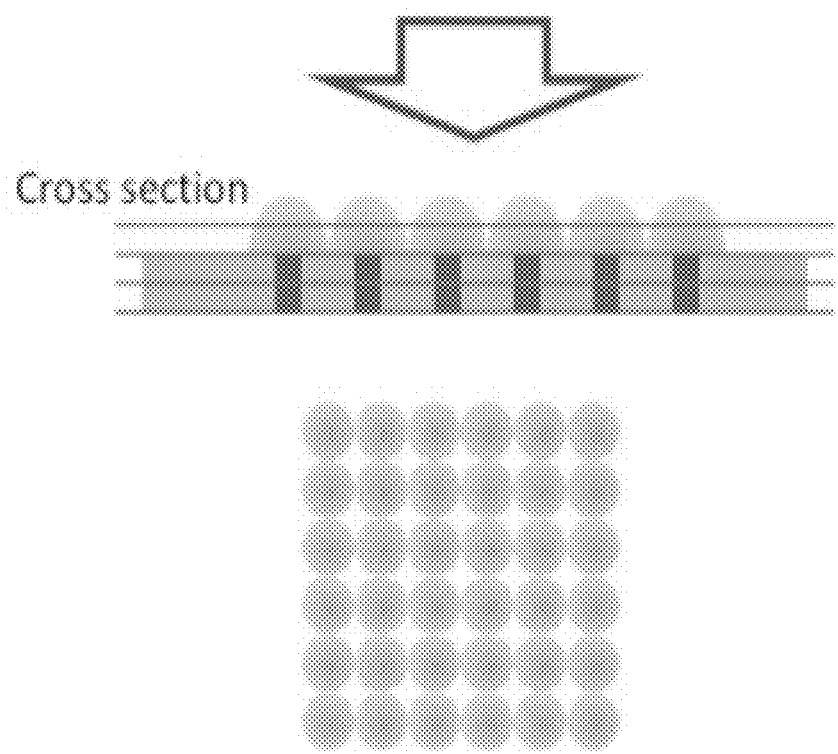

Methods:

A perforated membrane is placed on a 3% agar with thickness of 200 µm sliced with a vibratome. With reference to FIG. 26, the excised RWM (100) is placed on an agar (slice A, 200). Another agar (slice B, 202) is placed atop the RWM. Aqueous discontinuities such as bubbles are eliminated. Rhodamine B (1 mM) is poured on the bottom agar. By diffusion, the Rhodamine B will diffuse to agar B through the RWM. The agar on the top is removed and the amount of the Rhodamine Bin the agar is quantified with a fluorescent microscope (Zeiss Axiolab). Using a confocal microscope (Leica, TCS SP5 II), horizontal planes in the round window membrane are monitored to determine the flux of the fluorescent dye, based upon the increase of intensity of the fluorescent dye. The permeability can be calculated from the amount of flux.

Figure 28:
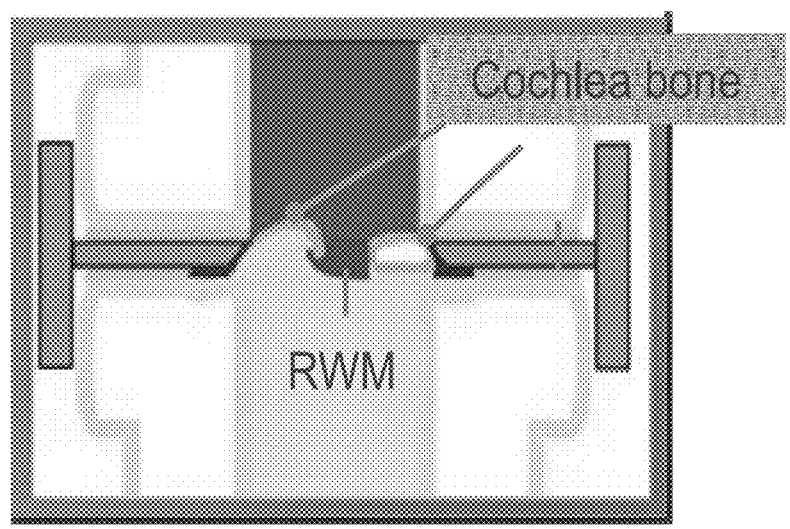
FIG. 28 is a schematic figure of a diffusion procedure in accordance with the disclosed subject matter.
Figure 29:
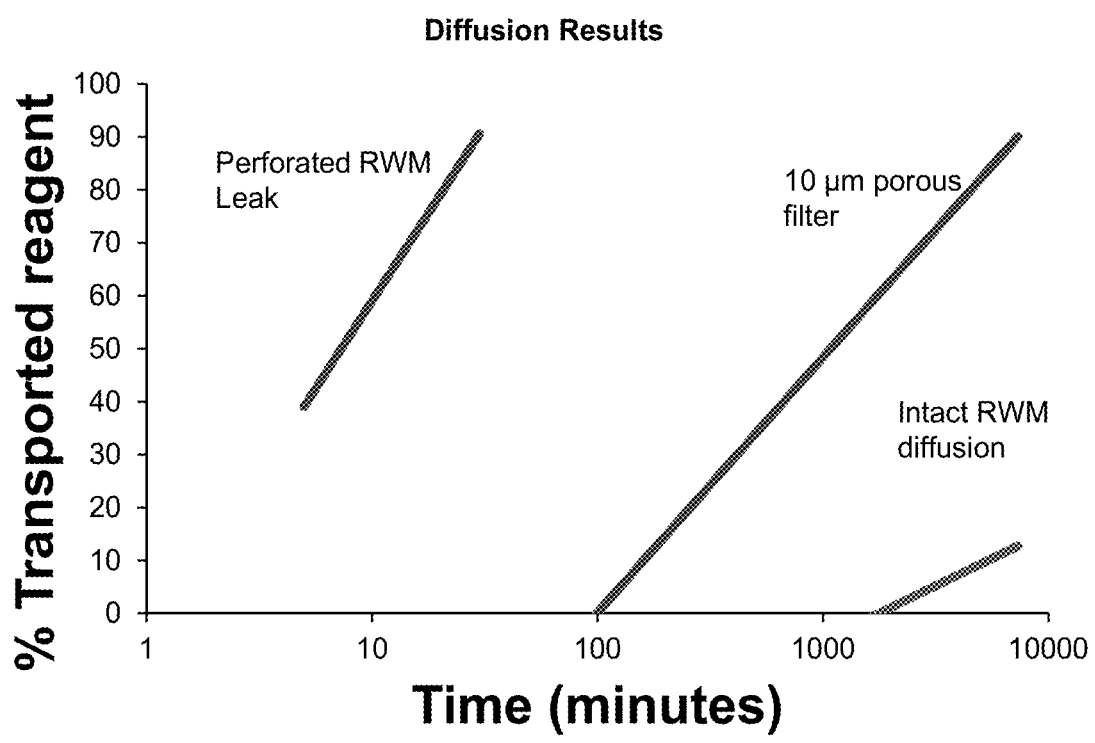
FIG. 29 is a graphical representation of a plurality of tests specimens: i) a perforated RWM leak; ii) a 10 μm porous filter; and iii) an intact RWM.

A Franz cell was employed to analyze the diffusion characteristics of the RWM, as shown in FIG. 28. Three different tests specimens were analyzed: i) a perforated RWM leak; ii) a 10 μm porous filter; and iii) an intact RWM. The results are shown in FIG. 29 which demonstrate that the perforated RWM has a significant reduction in diffusion time as compared to the 10 μm porous filter; and iii) an intact RWM.

Aim 4.3 In Situ Diffusion Study.

In accordance with another aspect of the disclosure, the permeation of fluorescent dye through the microperforation into the scala tympani in situ with cochlea bone is examined with confocal microscopy.

Methods:

A guinea pig cochlea is extracted and the RWM is exposed. The cochlea is fixed on a glass plate to make the RWM face vertically. The micro perforation is introduced by the developed methods with the micro-needle array, as described above. Under the confocal microscope, the focus plane is set just below the RWM. L of 0.1 mM Rhodamine B in perilymph solution is poured on the RWM. The flux of Rhodamine B can be measured and the permeability calculated.

This procedure can quantify the improvement of the permeability of the RWM of the Guinea Pig. The permeability of the perilymph solution is estimated from the diameter of the pore. The confocal microscopy itself can be a better option to determine the 3-D structure. However, in some embodiments, the fluorescent dye may be bound and immobilized to the membrane.

Aim 5. Characterization of the Anatomic and Functional Consequences of Using Micro-Needle Array to Create RWM Perforations and to Assess the Ability of Micro-Needles to Reliably Deliver Therapeutic Materials into the Cochlea Using Guinea Pig as an Animal Model.

Rationale.

The successful completion of above specific aims 1-4 aids in defining the optimal design of micro-needle array for testing in vivo. The guinea pig was chosen as the animal model because of ease of surgical access to the RWM. In this aim, perforations are created with the micro-needle array and characterize the length of time they stay patent, their effect of hearing, and their ability to enhance diffusion across the RWM.

Aim 5.1. Define the Histologic and Functional Consequences of Micro-Needle Array Introduced Micro-Perforations in the RWM.

Based on results from larger perforations, the healing process can be expected to close the micro-perforation of the RWM within 4-8 days. Thus, to determine the time course over which the micro-perforations close, the RWM are harvested immediately after the procedure, at 6 hours, 24 hours and at one week and two weeks. Additionally, tests for auditory function with auditory brainstem response testing (ABR) and distortion product otoacoustic emissions (DPOAEs) can be performed immediately after surgery, and then at 2, 7, 14, and 28 days after surgery.

Animal Surgery:

Animals are anesthetized with a combination of intramuscular ketamine (50 mg/kg) and the analgesic xylazine (9 mg/kg), and administered antibiotic prophylaxis using 4 mg of trimethoprim and 20 mg of sulfadiazine. Both RWMs are surgically accessed in all animals. A post-auricular incision is introduced with a few mm diameter opening of the bulla. Following a minimal bone removal in that area, the round window membrane is directly visualized. A stereotactically fixed stainless tube is introduced into the incision vertically toward the RWM. The micro needle loading surgical apparatus is introduced through the stainless tube. The RWM perforations are produced with the apparatus using the optimized variables from the in situ procedures.

Tissue Processing:

The animals are sacrificed with an intraperitoneal overdose of sodium pentobarbital (250 mg/kg) followed by bilateral thoracotomy. At the time of sacrifice, the animals are perfusion-fixed with a solution of 4.0% paraformaldehyde in 0.1 M phosphate buffer, pH 7.4. Temporal bones are harvested from both sides of the head. Each bulla are opened using rongeurs to expose the cochlea. The stapes are removed and the cochlea fixed by perfusion of 4.0% paraformaldehyde through the round window. The cochlea is then removed from the remaining temporal bone and immersed in 4.0% paraformaldehyde overnight at 4° C. After complete fixation, specimens are decalcified in 0.2M EDTA/1× PBS/4.0% paraformaldehyde for 2-3 weeks with at least three solution changes. Following decalcification, the specimens are placed in 0.9% saline, dehydrated through a graded alcohol series and then equilibrated in xylenes. Specimens are embedded in paraffin and sectioned at 6-8 μm on a microtome (Leica RM2035) for histology and immunohistochemistry.

Two *cochleae* from each sample group and time point are embedded in plastic for morphological evaluation of RWM. Briefly, the harvested *cochleae* is fixed in 2.5% glutaraldehyde in 0.1 M phosphate buffer. After 24 hours, the *cochleae* is rinsed with phosphate buffer, postfixed with 1% osmium tetroxide, and then dehydrated in a graded series of ethanol, transferred to propyleneoxide, and embedded in plastic (Agar 100 Resin kit, Agar Scientific).

After polymerization and removing the bone adjacent to the RWM, the area of round window niche with the RWM is re-embedded on a blank block of Agar 100 to allow sectioning perpendicularly to the membrane. The specimens are sectioned at 2.5 m thickness using a microtome (LKB Ultramicrotome system 2128 Ultrotome). Thin sections are mounted on glass slides and stained with 0.1% toluidine blue. The RWM thickness is measured using a light microscope (Zeiss Axiolab) equipped with a digital camera (Altra 20 soft imaging system, Olympus) and image analysis software (Cell, Olympus). Measurement of three sections of each RWM is made at the mid portion of each membrane, and the mean value is calculated. For electron microscopy, ultra thin sections are obtained, mounted on copper grids, and stained with uranyl acetate and lead citrate. Grids are examined with a Phillips CM12 Transmission Electron Microscope and photographed with a 1 k×1 k Gatan CCD Camera.

Histology and Immunohistochemistry:

The cochlear paraffin sections for immunochemistry are prepared as previously described. Briefly, the paraffin-embedded cochlear sections is dewaxed, blocked with 10% NHS, 0.1% Tween 20 in PBS and then hybridized overnight with the relevant primary antibody. Presence of cell-mediated immune response is characterized using antibodies against the guinea pig T4 lymphocytes (anti-CD45 antibody, clone no. IH-1) and macrophages (anti-LI antibodies, clone no. MAC387). Both of these antibodies are commercially available through Serotec Inc, Raleigh, N.C. The hybridized sections is then be processed as described above.

Auditory Brainstem Response (ABR) Testing:

Following administration of anesthesia, responses are recorded from silver wire electrodes inserted through the skin at the vertex (negative), ipsilateral mastoid (positive) and contralateral mastoid (ground). The scalp-recorded potentials are amplified and sampled at a rate of 10 kHz by an analogue to digital converter using Tucker-Davis software. The clicks or tones (4, 8, 16 and 32 KHz) are presented at a rate of 33 per second and the responses averaged over 500 trials. The ABR threshold to a broadband (click) stimulus are established for both ears. At near-threshold stimulus levels, recordings are repeated to test the consistency of wave identification. For both ears, the ABR threshold at each frequency is defined, as the stimulus needed to produce a visual detection of at least one of the waves observed in response to a broadband click stimulus. Data is statistically evaluated by Student's t-test and by ANOVA with Tukey's or Newman-Keuls post-hoc test.

Otoacoustic Emission Testing:

Following administration of anesthesia, Distortion Product Otoacoustic Emissions (DPOAEs) at 2 $f_1$-$f_2$ is elicited from both ears using a Tucker Davis Technologies (Gainesville, Fla.) System II. Two equivalent level ($L_1$=$L_2$) primary signals ($f_1$ and $f_2$) with $f_2/f_1$=1.3, are generated and test frequencies will range from 2 to 18 kHz. The primary tones produced by two separate speakers (modified Super Tweeter 40-1310B Tandy Corporation, Fort Worth, Tex.) is introduced into the animal's sealed ear canal through an insert earphone speculum. DPOAE recordings are made with a low-noise microphone (Etymotic Research, ER 10BDetection threshold and supra-threshold measures in the form of input/output (I/O) functions are obtained by decreasing the primary tones from 85 to 25 dB sound pressure level (SPL), in 5-dB steps. An emitted response is identified as positive if the DPOAE at $2f_1$-$f_2$ is 3 dB above the noise floor level. Statistical significance of differences between the control and experimental cochlea is determined using Fisher's least square difference and Scheffe's F-test.

Aim 5.2 to Characterize the Diffusion of Therapeutic Reagents Through Micro-Needle Array Introduced Micro-Perforations in the RWM.

Rational:

The permeability of gentamicin through the RWM of Guinea pig is determined in vivo. An analysis of how the introduction of the micro-perforations impacts or enhances permeability is provided. The amount of the gentamicin delivered into the scala tympani is determined and the ratio between the amount collected and administered is quantified as delivery efficacy. In some embodiments, the effect of the artificial modification to the endogenous permeability of the RWM lasts for a few hours. Thus, this acute procedure is suitable to show the permeability improvement and independency before the endogenous healing process affects the perforation.

Methods:

Application of Drug to RWM.

Immediately after the introduction of micro perforation, gentamicin (Refobacin 40 mg/mL, Merck, Darmstadt, Germany) is applied in a continuous drip to the RWM from a pipette placed close to the bony lip of the round window (RW) niche for 1, 2, and 3 hours. The rate of drug irrigation is 5 µL/min in the 30-minute experiments, 4 µL/min in the 2 hour experiments, and 5 µL/min reduced to 2 µL/min after the first hour in the 3 hour experiments. The intracochlear fluid is sampled from a small opening made in the apical turn of the cochlea. To collect all of the fluid without any loss to the middle ear, a cup made of a two-part silicone adhesive (Kwik-Cast, World Precision Instruments, Sarasota, Fla.) is constructed around a small portion of exposed apex site at the apex. To sample effusate, an incision is made in the silicone cap with a pick. Perilymph solution emerging from the incision is collected sequentially 10 times with glass capillary tubes. Each collected sample is approximately 1 µL.

Quantification of Gentamicin.

Each sample is diluted with 120 µL of Abbott Labs IVD 9519 dilution buffer. Gentamicin is quantified with a fluorescence-polarization-immunoassay (TDX SLX Analyzer, Abbot, Abbott Park, Ill.). The permeability of the RWM is determined using the FEM software obtained at http://oto.wustl.edu/cochlea/. The concentration of gentamicin is simulated and the permeability is changed until the calculated concentrations best fits with the 10 samples from each procedure.

Additional Exemplary Embodiment

Figure 30:
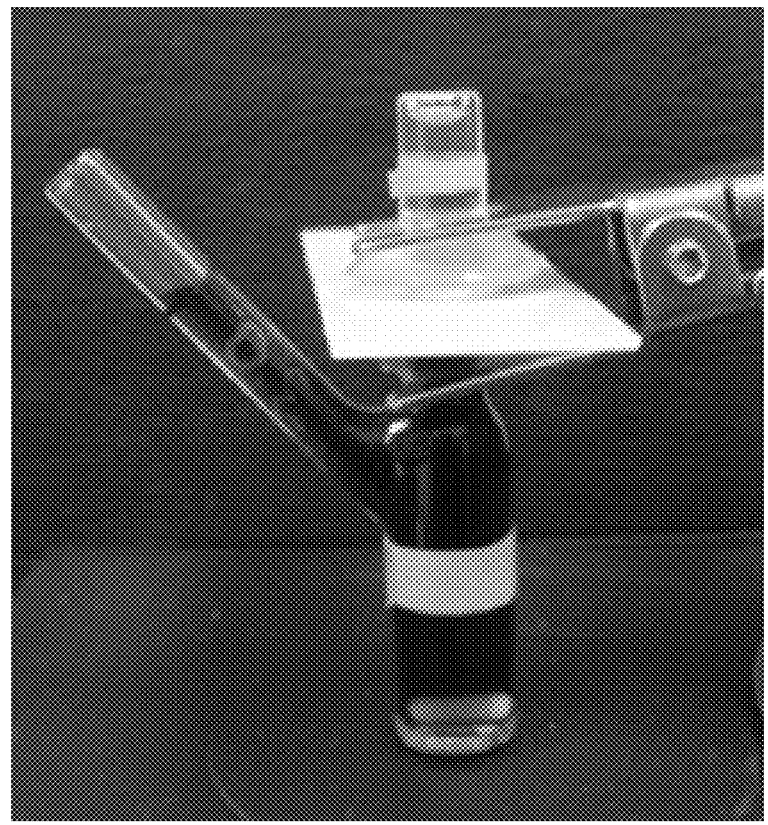
Figure 31:
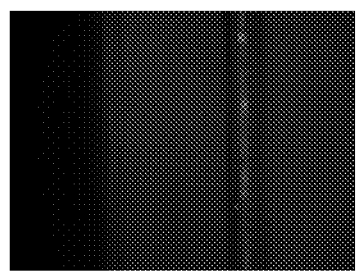
FIG. 31 is an exemplary view of fluorescent light microscopy in accordance with an aspect of the present disclosure.
Figure 32:
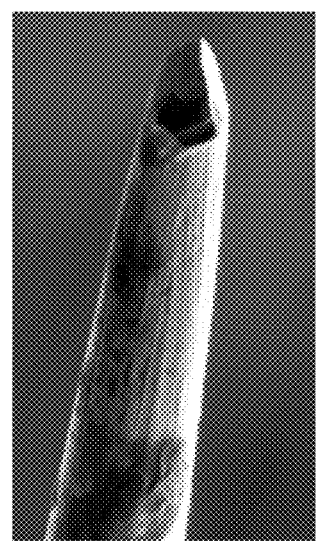
FIG. 32 is a zoom-in view of a 10 μm diameter needle.

In another embodiment, a model for measuring diffusion across a guinea pig RWM, was developed and tested. The model is applicable for analysis of the RWM both with and without microperforations. Semicircular canals were removed from the pigs and RWM exposed prior to perforation. In the exemplary embodiment, the cochlea, sparing the RWM, was embedded in a 3D-printed acrylic holder using hybrid dental composite and light cured to adapt the round window niche to a 3 ml Franz™ Cell. The Franz™ Cell is a widely recognized standardized method for studying transdermal drug delivery. An illustration of this Franz™ Cell is provided in FIGS. 30 and 33A. Microperforations were created with a 10 µm diameter needle (as shown in FIG. 32) and examined with fluorescent light microscopy (FSX-100, as shown in FIG. 31) as a function of time exposure. In one instance, diffusion of 500 µM rhodamine B across the RWM in a Franz™ Cell was measured via fluorescence microscopy employing an antibiotic (e.g. Gentamicin Analog, MW 479.01 g/mol) and fluorescent molecule (e.g. Rhodamine B or "RhoB").

Figures 34A, 34B:
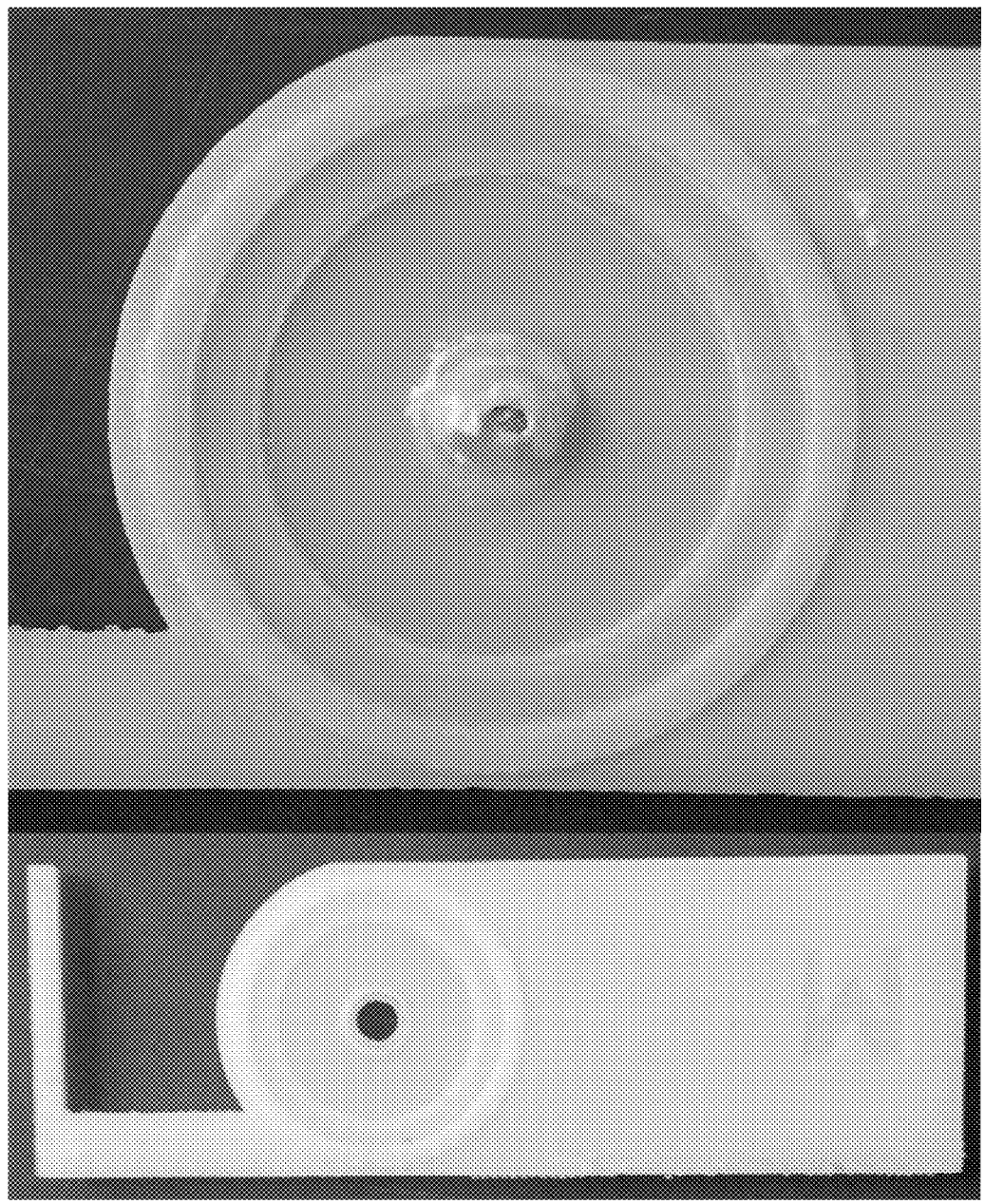
FIGS. 34A-B are an exemplary illustrations of a customized adaptor to a standard Franz™ Cell in accordance with an aspect of the disclosure.

In the exemplary embodiment show in FIGS. 33-34, a Franz Cell was customized in accordance with the present disclosure to include an adapter to allow analysis of a very small membrane in the Franz Cell. The adaptor depicted in FIGS. 33B and 34 was manufactured with a 3-dimensional printer, though alternative manufacturing techniques (and suitable materials) are contemplated to be within the scope of the disclosure. The adaptor includes a downwardly extending protrusion or lip (see reference numerals "A" and "B" in FIG. 33) which are configured to engage the Receptor portion of the Franz Cell.

Figures 37A, 37B, 37C:
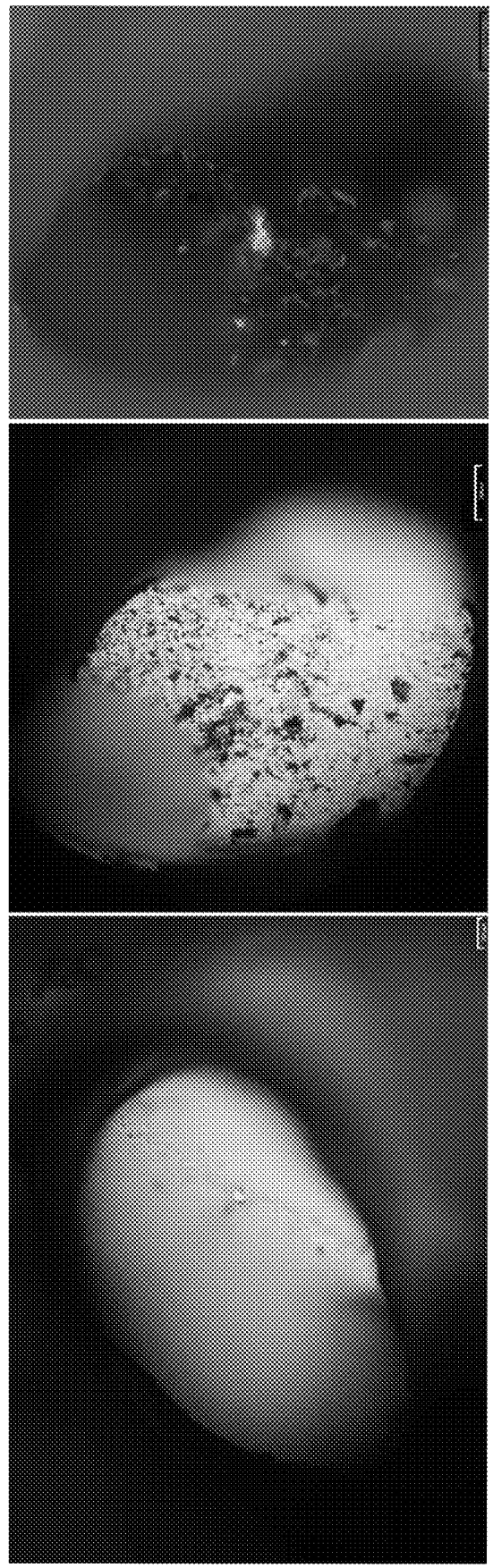
FIGS. 37A-C and 38 are images of exemplary results in accordance with the present disclosure.
Figure 38:
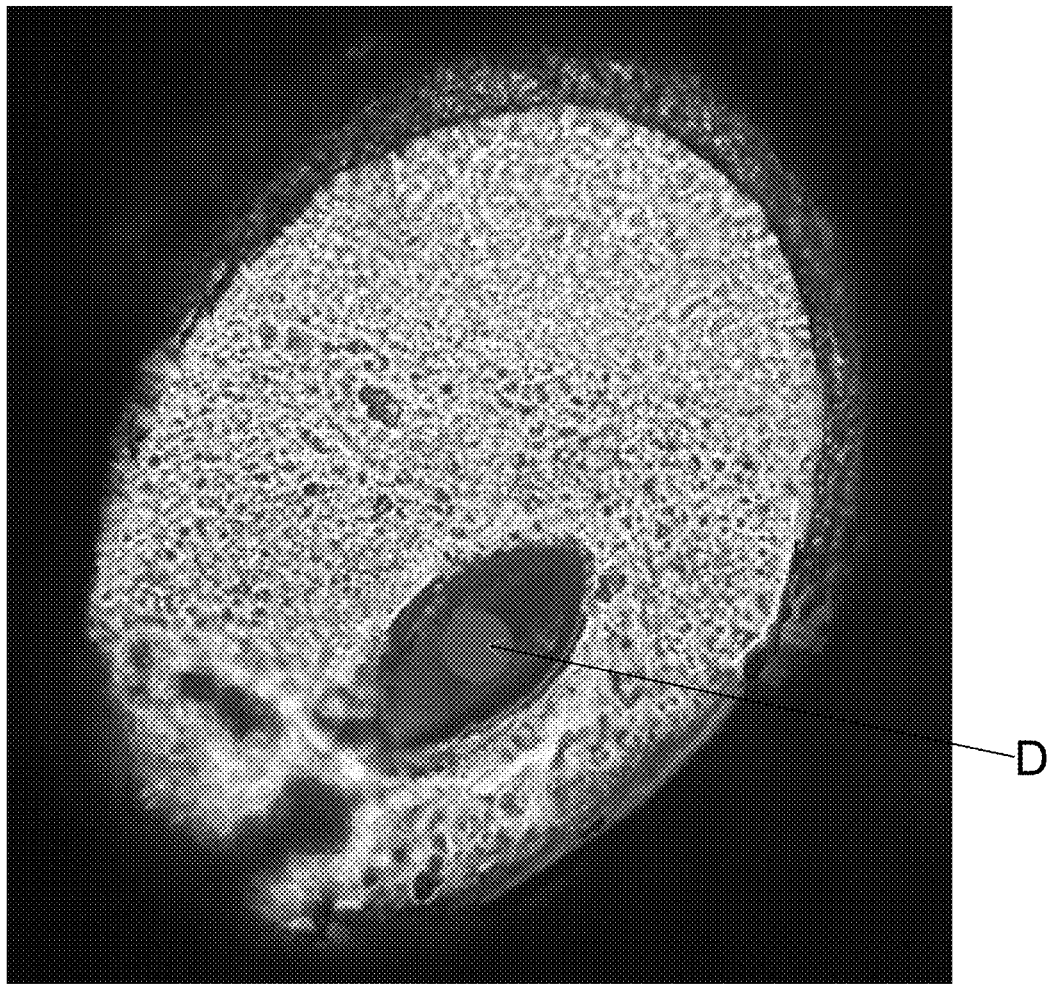

A series of data points were tested, the results of which are provided in FIGS. 35 and 36. Similarly, FIGS. 37A-C illustrate various Z-stacked perforation images which were compiled from 60 images taken at 5 µm intervals of RWM with perforation: A) bright field microscopy; B) bright field microscopy post diffusion with RhoB; C) Fluorescent microscopy Manual perforations made with 10 µm needle tip produce an elliptical hole (see arrow in FIG. 38) with axes 30 µm (26-34)×47 µm (44-50). In one example, a manual perforation with 100 µm needle tip created an elliptical tear in the membrane Measuring 240 m×460 µm, as shown in FIG. 38 (in which the dot "D" indicates tip size).

Figure 39:
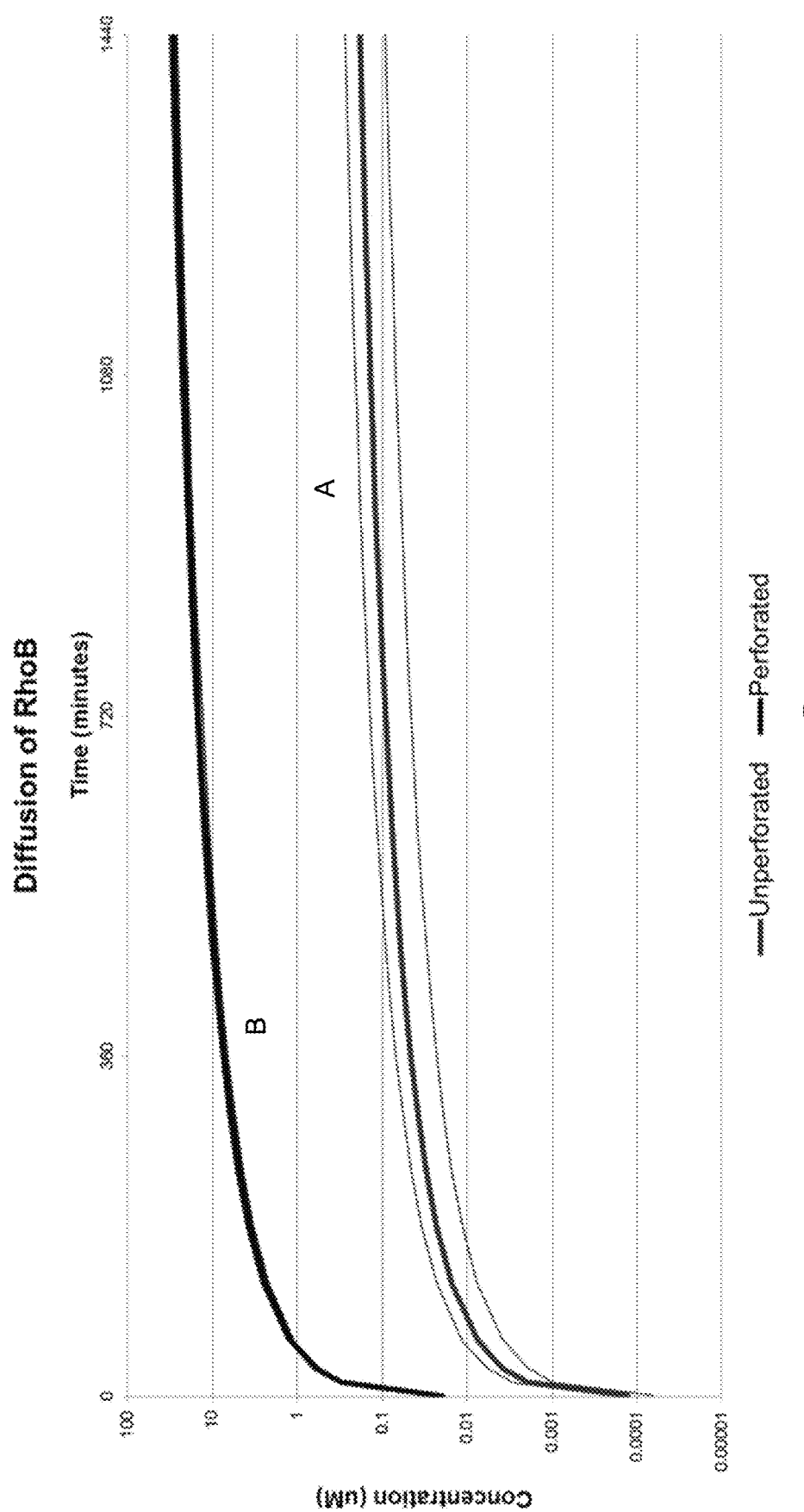
FIG. 39 is a graphical plot of diffusion of Rhodamine B.

In accordance with an aspect of this disclosure, an enhancement of diffusion can be shown as permeability of RWM increased from: Unperforated KP of $2.01 \times 10^{-8}$ m/s (95% CI: $9.98 \times 10^{-9}$ m/s-$3.04 \times 10^{-8}$ m/s) to a Microperforated KP of $3.21 \times 10^{-6}$ m/s (95% CI: $2.91 \times 10^{-6}$ m/s-$3.52 \times 10^{-6}$ m/s) (where T-test (equal variances) p<0.05). A graphical plot of diffusion of RhoB is provided in FIG. 39 wherein the thick line indicates average, and the thin lines indicate 95% Confidence Interval (with "A" referencing Unperforated samples and "B" representing Perforated samples). Accordingly, the 100 μm needle produced a 240 m×460 μm elliptical perforation in the membrane and was associated with a 3500× enhancement* in diffusion (*p<0.05). The 10 μm needle produced a 30 m×47 μm perforation and was associated with a 160× enhancement* in diffusion (*p<0.05).

The results obtained herein demonstrate macroperforation needle proportional to a 30 gauge needle perforation in a human round window membrane. Additionally, the results obtained herein indicate it would require 3.7 years to reach 250 μM (½ the concentration of drug applied to the membrane) in an unperforated membrane, while it would require only 8.5 days in membranes with a small microperforation. These findings have significant therapeutic potential for the treatment of pathological processes affecting the inner ear. In this exemplary embodiment, perforations were introduced manually and produced consistent hole sizes in each sample. However, perforations were found to cause tears in the membrane, as indicated by the elliptical shape and increased size compared to the needle tip. Accordingly, this techniques and results obtained herein demonstrates the need for microneedle design to be based on the mechanical properties of the membrane to provide precise perforations to the round window membrane.

Additional Exemplary Embodiment

The diffusion across guinea pig RWM, with and without microperforation, was developed and tested: *cochleae*, sparing the RWM, were embedded in 3D-printed acrylic holders using hybrid dental composite and light cured to adapt the round window niche to 3 ml Franz diffusion cells. Perforations were created with 12.5 μm diameter needles and examined with light microscopy. Diffusion of 1 mM Rhodamine B across RWM in static diffusion cells was measured via fluorescence microscopy.

The diffusion cell apparatus provided reliable and replicable measurements of diffusion across RWM. The permeability of Rhodamine B across intact RWM was $5.1 \times 10^{-9}$ m/s. Manual application of microperforation with a 12.5 μm diameter tip produced an elliptical tear removing 0.22±0.07% of the membrane and was associated with a 35× enhancement in diffusion (p<0.05).

Consequently, diffusion cells can be applied to the study of RWM permeability in vitro. Microperforation in RWM is an effective means of increasing diffusion across the RWM.

In order to carry out this analysis, diffusion of RhoB through the RWM was performed on 12 Hartley Strain Guinea Pigs in a modified diffusion cell at room temperature. Franz™ Cell-type diffusion cells (PermeGear, Inc., Hellertown, Pa.) are made of borosilicate glass and have a 5 mm orifice and a 3 ml receptor volume with flat ground joints (FIG. 30). The cell consists of three parts (FIG. 33): donor chamber, membrane, and receptor chamber.

Donor Chamber.

The donor chamber was filled with 0.3 ml of 1 mM RhoB in PBS meeting the conditions for continuous infinite dosing. Donor chamber was covered with Parafilm® for the duration of the experiment. Drug application surface was determined by size of RWM.

Membrane.

Guinea pig RWM was embedded in an acrylic holder with dental composites (FIG. 34). The acrylic holder was designed and 3D printed (Objet 24, Stratasys, MN) to allow for adaptation of the round window niche containing RWM to the diffusion cell. Dental composites (Dentsply, Milford, Del.) included primer (Prime & Bond® NT™) and a urethane modified Bis-GMA resin (TPH Spectra™) which were light cured at 20 s intervals with a 470 nm light emitting diode greater than 500 mW/cm². The diffusion cell was assembled with two custom expanded Polytetraflurane (PTFE) gaskets, 1.5 mm thick, to prevent leakage from the donor or receptor chambers at the diffusion cell/membrane interface. The acrylic holder was tested for reactivity with RhoB and was inert for >48 hours. The RWM was equilibrated in PBS solution for 30 minutes prior to application of RhoB. Membranes were embedded and equilibrated within 2 hours of euthanasia.

Microperforations were introduced in the RWM with manual application of a minutien insect pin (Size 000, 12.5 μm diameter tip, 250 μm diameter shaft) under a binocular microscope. All membranes were imaged before and after diffusion study using bright field, phase contrast or fluorescent microscopy and Z-stacking. Imaging was used to confirm the presence or absence of membrane perforation. 60 images at 5 m intervals were taken and compiled to create one image. ImageJ (Rasband, W. S., Image J, U.S. National Institutes of Health, Bethesda, Md.) was used to calculate the size of the membrane and, if present, perforation.

Receptor Chamber.

The receptor chamber was filled with 3 ml of PBS and continuously stirred at 650 rpm with a cylindrical Teflon® magnetic stirbar to allow rapid mixing of contents without development of a vortex. Sampling port allowed for extraction of fluid samples at various time points to monitor progression of diffusion. The set up and sampling conditions were validated for consistency in the following categories: 1) diffusion cell dimensions, 2) stir bar speed, and 3) sampling frequency, to increase the precision of results across experiments[23]. Sink conditions, defined as concentration in the receptor chamber <10% solubility concentration, were satisfied at all times during the experiment.

Sampling of the receiver chamber was made at 12 predetermined times over 24 hours and analyzed with fluorescent microscopy. At each time point 90 μL was removed using a stretched syringe from the center of the receptor chamber and the volume was replaced with 90 μL of fresh PBS. These diffusion experiments are considered static as solution from the receptor chamber is renewed by removal of a set quantity (90 μL) at sampling times and replacement of this volume with fresh medium. The removed 90 μL was then diluted with 360 μL PBS to reduce the effects of evaporation and maintain concentrations within the acceptable detection range of the microscope. The samples were placed on a tilt table to enhance mixing after dilution. Right and Left *cochleae* were run in parallel.

Quantitative Analysis of Rhodamine B.

Samples from each time point were sealed in 0.6 mm square capillary tubes to allow detection with fluorescent microscopy. Tubes were sealed to a glass microscope slide with Norland Optical Glue 63. Square capillary tubes allow direct measurement of fluorescence without distortion of light. Samples were imaged with a Bio Imaging Navigator FSX-100 fluorescent microscope. Three samples taken at each time point were imaged and averaged. Calibration curves were constructed using standards of RhoB concentrations between 0.01 μM and 10 μM.

Statistical Analysis.

Statistical analysis was performed with Microsoft Excel. All data are presented as their mean±standard deviation (SD). Least squares regression analysis was performed to determine the slope and standard errors (SE) of sample data. F-tests were performed to assess for equal variance prior to conducting a two sample T-test, two tails, alpha=0.05, for equal or unequal variance (as determined by F-test) between perforated and unperforated samples. Statistical differences were considered significant at the p<0.05 level. The coefficient of variance (CV) was calculated to assess variability of measurements:

$$C_v = \frac{\sigma}{\mu} \quad (1)$$

Results

Adaptation of Diffusion Cell Method

The diffusion cell was adapted to the size and shape of the RWM using an acrylic adapter. The additional height of the RWM niche necessitated the use of thicker gaskets to provide a watertight seal. Expanded PTFE gaskets (1.5 mm thick) were able to seal the diffusion cell to the adapter without reacting to the test substance. Additionally, a new clamp was built to hold together the components of the diffusion cell while providing enough force to compress the PTFE gaskets.

Permeability of RWM to Rhodamine B.

Figure 40:
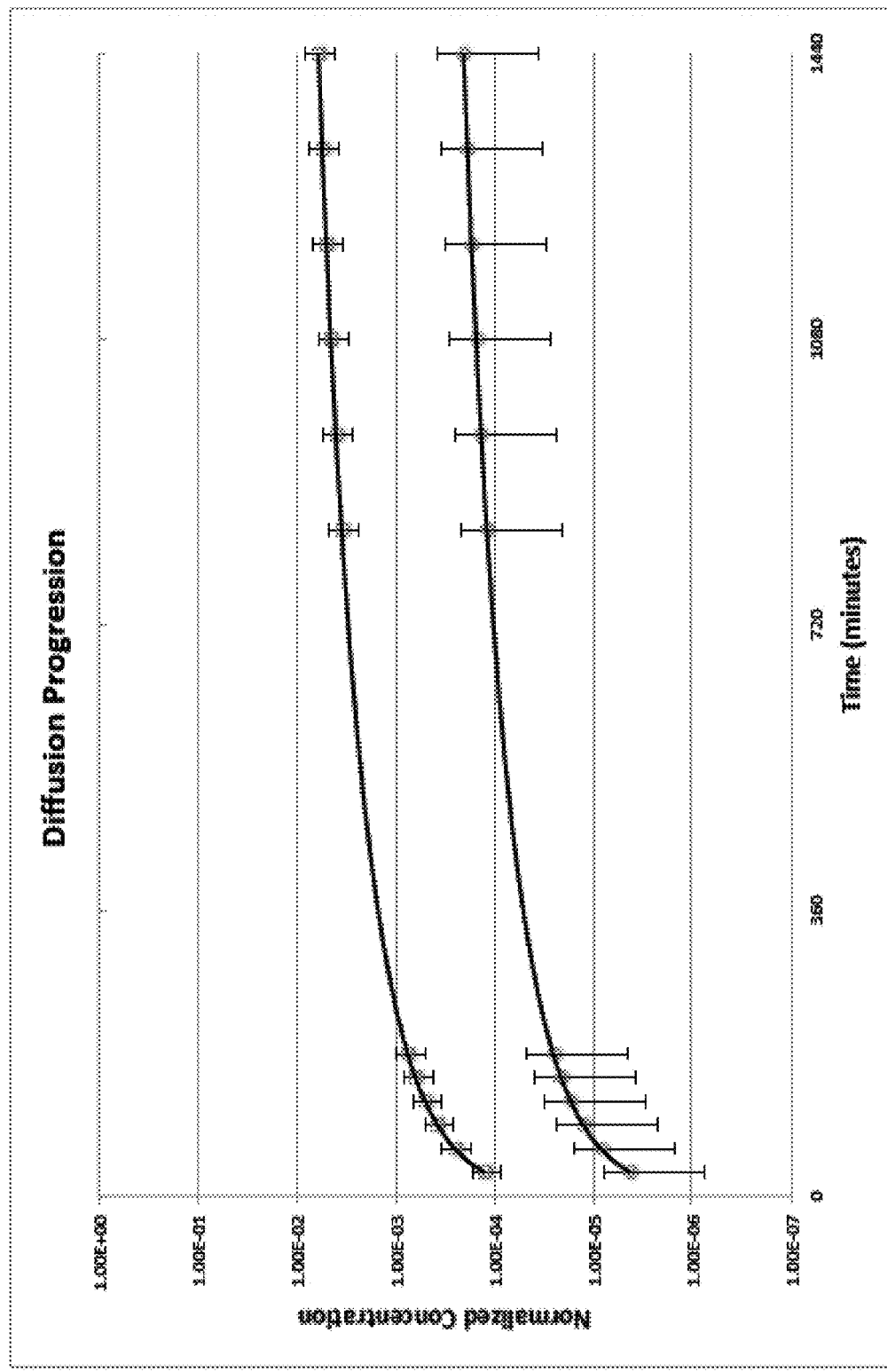
FIG. 40 is a graphical plot of the progression of the diffusion with the normalized concentration as a function of time for the perforated (squares) and unperforated (circles) membranes. Error bars indicate standard deviation.

1 mM RhoB solution was applied to the RWM and concentration of RhoB in the receptor chamber was measured overtime. RhoB concentration increased with time as RhoB entered the receptor chamber through the RWM to reach steady-state concentration. The diffusion of RhoB across intact RWM in a diffusion cell setup was monitored for up to 24 hours (n=6). The diffusion progression is shown in FIG. 40.

A linear regression was used to model the change in quantity over time of RhoB. The permeability coefficient (KP) was derived from this regression by $$K_P = \frac{Q}{A \cdot t \cdot (C_o - C_i)} \quad (2)$$

where Q is the mass (pg) of compound transported through the membrane in time (t) across area of exposed membrane (A). $C_o$-$C_i$ are the concentrations on the outer (donor) and inner (receptor) side of the membranes and can be simplified to $C_o$ in infinite dosing conditions. The permeability of the RWM to RhoB was determined to be 0.51±0.41×10$^{-8}$ m/s. Animals in this group had a coefficient of variance of 80%. Results are summarized in Table 3.

Application of Microperforations.

The RWM was imaged and sized with bright field microscopy to determine surface area of diffusion and relative size of perforations. RWM size overall was 1.19±0.17 mm$^2$ (n=12; CV 14%). No statistically significant difference in size of membrane was seen between the unperforated and perforated groups (Table 4). Perforations were elliptical, 2.53±0.73×10$^{-3}$ mm$^2$ (n=6; CV 29%) (Table 5).

Permeability with Microperforations.

Diffusion experiments were carried out on RWM samples after manual creation of microperforations. The procedure of the diffusion experiment in perforated group was identical to unperforated group. The permeability coefficient of the RWM with microperforations was measured at 18.1±6.1×10$^{-8}$ m/s with a coefficient of variance of 34%. This represents a statistically significant increase in permeability of 35 times with 0.22% microperforation in the round window membrane. F-test showed equal variance between groups; Two Tailed T-test for equal variances performed with alpha 0.05, p<0.05 (Table 4).

This disclosure focuses on the methodology and enhancement of drug delivery to the inner ear. After adapting the standardized static diffusion cell method to the study of inner ear drug delivery, this method was applied to the study of microperforations as a means of permeability enhancement. RWM is permeable to a large range of materials, including various antimicrobials, steroids, anesthetics, tracers, albumin, horseradish peroxidase, latex spheres, germicidal solutions, water, ions and macromolecules. The extent of permeability to these various materials is dependent on the size, charge, liposolubility and morphology of the compound as well as RWM thickness. The adapted Franz cell method provides astandardized, controlled means to study permeability enhancers, both pharmaceutical and surgical, on the RWM. This method can also be applied to the study of drug release formulations with new models that extrapolate the standard diffusion cell to the unique physical dimensions of the cochlea.

The observed RWM permeability coefficient to RhoB is smaller than those seen in previous studies for gentamicin and dexamethasone (Table 3). This is consistent with the lower diffusion coefficient of RhoB and may also be attributed to significant variability in RWM permeability. In addition to its similarity to medicines routinely used in the ear, RhoB is also relatively inexpensive and easy to detect and measure in small concentrations. While an increase in permeability with macroperforation (>1%) has been shown in the past, a potential concern of pores within the RWM is leakage of perilymph from the scala tympani into the middle ear due to perilymph pressure. A micropore, by nature, is suited to prevent perilymph leakage without slowing the diffusive transport of therapeutic reagents. In smaller pores, the viscous resistance to the fluid flow due to the close presence of the walls of the pore causes a decrease in the flow rate. In other words, the Reynolds number, which is the ratio of the inertial forces to the viscous forces in the flowing fluid, quantifies this behavior. A small Reynolds number due to large viscous forces leads to laminar rather than turbulent flow of liquid through a pore. Under such circumstances, the fluidic resistance of a circular pore is inversely proportional to the 4th power of the pore diameter. Thus, decreasing a pore diameter by a factor of 10 while increasing the number of holes by 100 times to keep the total area constant, increases the fluid resistance 100 times; this is one of the reasons why a design with multiple smaller perforations is preferred instead of one large hole.

Permeability with a single microperforation was 35 times that of an intact RWM, with permeability across the perforation itself at 8.3±2.2×10$^{-5}$ m/s (CV 26%), 16,000 times the permeability across an intact membrane (Table 4). This change is the same magnitude as the predicted value of 4×10$^{-5}$ m/s based on the diffusion coefficient (Table 3). Ototoxicity from aminoglycosides is seen with 10 μM of compound. With the dosing regimen seen in this experiment applied to the RWM, an intact membrane would require 7 days to diffuse 10 μM across the RWM while a membrane with a single microperforation of approximately 2.5×10$^{-3}$ mm$^2$ would require just under 5 hours. Assuming minimal interaction between perforations, an increase in the number of perforations will inversely decrease time necessary to achieve target dose. A three perforations are expected to reach 10 μM in 1.5 hours, and a 3×3 array of perforations in only 30 minutes, a time span more consistent with the capabilities of surgical administration of medication to the RWM and new delayed and continuous release drug formulations.

The coefficient of variance among intact RWM samples (80%) was higher than the recommended value of <30% capable with diffusion cell studies. We recommend the use of barrier integrity measurements in future studies. Variability in measured permeability results of intact membranes may be from desiccation of the membrane and consequent damage to the epithelial layer during preparation or imaging despite precautions taken to protect the membrane during these steps. The RWM is a three-layered membrane composed of an outer epithelial layer, thick middle fibrous collagen layer and inner epithelium. Both the outer and inner epithelial layers play a role in the diffusion of molecules across the RWM, ranging from passive diffusion to pinocytosis. Of note, the coefficient of variance was significantly lower (34%) in perforated samples, which may represent either an alternate method of diffusion compared to the intact membrane or simply the minuteness of the variation at a significantly higher permeability.

Microperforations were manually applied withease and created irregular tears of similar sizes. Studies on the mechanical properties and shape of the RWM may be able to create more reliable perforations in the RWM. The RWM is known to spontaneously heal from large perforations. By creating microperforations, we may be able to transiently increase the permeability of the round window membrane while reducing the possibility of complications (infection, perilymph leakage) due to the natural healing properties of the membrane. In vivo application of microperforations with varying healing times followed by in vitro diffusion across RWM and histology would provide insight into the healing capabilities of RWM. Investigations into the timescale of microperforation healing, and the creation of precise holes rather than tears may allow the introduction of a transient, self-healing opening into the cochlea for controlled drug delivery. The findings of our study open the door to novel manipulation of the RWM for the treatment of inner ear diseases.

TABLE 3

Permeability of Gentamicin, Dexamethasone and Rhodamine B

|  | Molecular Weight (g/mol) | Diffusion Coefficient in water at 25° C. (298 K) ($10^{-6}$ $cm^2 s^{-1}$) | Permeability $K_P$ RWM ($10^{-8}$ $ms^{-1}$) | Estimated Permeability $K_P$ PORE ($10^{-5}$ $ms^{-1}$) |
|---|---|---|---|---|
| Gentamicin | 477.60 | 6.82 | 5~35 | 6.82 |
| Dexamethasone | 392.46 | 7.20 | 3.5 ± 4.6 | 7.20 |
| Rhodamine B | 479.01 | 4.5 ± 0.4<br>4.27 ± 0.04 | 0.51 ± 0.41 | 4.5<br>4.27 |

TABLE 4

Summary of Membrane and Perforation Size Characteristics and Permeability Coefficient ($K_P$)

|  | Size ($mm^2$) | Perforation ($10^{-3}$ $mm^2$) | Perforation (%) | $K_P$ RWM ($10^{-8}$ $ms^{-1}$) | $K_P$ PORE ($ms^{-1}$) |
|---|---|---|---|---|---|
| Unperforated (n = 6) | 1.24 ± 0.24 | N/A | N/A | 0.51 ± 0.41 * | N/A |
| Perforated (n = 6) | 1.17 ± 0.05 | 2.53 ± 0.73 | 0.22 ± 0.07 | 18 ± 6.1 * | 8.3 ± 2.2 × $10^{-5}$ |

* Statistically significant p < 0.05

TABLE 5

Membrane and Perforation Characteristics of Perforated RWM

| # | Size ($mm^2$) | Perforation ($mm^2$) | Perforation (%) | $K_P$ PORE ($10^{-5}$ $ms^{-1}$) |
|---|---|---|---|---|
| 1 | 1.19 | 0.00142 | 0.119 | 6.82 |
| 2 | 1.18 | 0.00241 | 0.204 | 9.65 |
| 3 | 1.23 | 0.00294 | 0.238 | 11.1 |
| 4 | 1.12 | 0.00348 | 0.311 | 5.10 |
| 5 | 1.05 | 0.00288 | 0.273 | 7.75 |
| 6 | 1.10 | 0.00204 | 0.186 | 9.45 |

While the disclosed subject matter is described herein in terms of certain preferred embodiments, those skilled in the art will recognize that various modifications and improvements may be made to the disclosed subject matter without departing from the scope thereof. For example, while the exemplary embodiment(s) disclosed above are directed to cochlear applications, the disclosed subject matter could also be configured for use with the eye, middle ear, brain or other thin membranes within the body.

Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A medical device capable of creating temporary perforations in a round window membrane of an inner ear, comprising:
a plurality of micro-needles on a base adapted to mount onto a surgical instrument configured to access the round window membrane via the tympanic membrane or via the mastoid process and position the microneedles proximate the round window membrane, wherein the surgical instrument comprises a driver, introducer or catheter configured to operate to insert the microneedles into the round window membrane to a desired depth; wherein the base is configured as a portion of an osculating sphere with a radius equal to the curvature radius of the round window membrane along its minor axis.

2. The medical device of claim 1, wherein the plurality of micro-needles are arranged in an array.

3. The medical device of claim 1, wherein the plurality of micro-needles are made of silicon.

4. The medical device of claim 1, wherein at least one of the plurality of micro-needles is hollow.

5. The medical device of claim 4, wherein the plurality of micro-needles include a lumen for delivering a therapeutic agent into the perforations.

6. The medical device of claim 1, wherein at least one of the plurality of micro-needles includes a solid cross-section.

7. The medical device of claim 6, wherein the at least one of the plurality of micro-needles include a therapeutic agent disposed on an exterior surface of the at least one of the plurality of micro-needles.

8. The medical device of claim 1, wherein at least one of the plurality of micro-needles includes a tip with a distal end, the distal end of the tip is tapered to a diameter of about 0.5 microns.

9. The medical device of claim 8, wherein the tapered tip includes a gradual taper.

10. The medical device of claim 1, wherein the plurality of micro-needles includes a first micro-needle and a second micro-needle, the first micro-needle includes a first length and the second micro-needle includes a different second length such that a non-uniform perforation design is obtained by the medical device.

11. The medical device of claim 1, wherein the respective one of the plurality of micro-needles includes a diameter of about 20 microns.

12. A system for delivering therapeutic agent to an inner ear of a subject comprising:
at least one surgical instrument configured to access a round window membrane via the tympanic membrane or via the mastoid process; and
a plurality of micro-needles on a base adapted to mount onto the surgical instrument, wherein the surgical instrument comprises a driver, introducer or catheter configured to position the microneedles proximate the round window membrane and operate to insert the microneedles into the round window membrane to a desired depth,
wherein the base is configured as a portion of an osculating sphere with a radius equal to the curvature radius of the round window membrane along its minor axis, and
wherein the plurality of micro-needles is configured to be detachably removable from the at least one instrument.

13. The system of claim 12, wherein the system is disposable.

14. The system of claim 12, wherein at least one of the plurality of micro-needles includes a hollow lumen.

15. The system of claim 14, further comprising:
a reservoir including a therapeutic agent.

16. The system of claim 15, further comprising at least one of a syringe or an osmotic pump configured to deliver the therapeutic agent from the reservoir to the at least one of plurality of the micro-needles.

17. The system of claim 14, further comprising an aspirating lumen within at least one micro-needle fluidly connected to a pump that provides suction for aspirating the round window membrane.

18. The system of claim 12, wherein the plurality of micro-needles is retracted from the round window membrane perforations prior to dispensing the therapeutic agent.

19. The system of claim 12, wherein the diffusion of Rhodamine B across a round window membrane perforated with a 10 µm-diameter needle is enhanced 160-fold compared to a non-perforated round window membrane.

20. The system of claim 12, wherein the plurality of micro-needles includes a first micro-needle and a second micro-needle, the first micro-needle includes a first length and the second micro-needle includes a different second length such that a non-uniform perforation design is obtained by the medical device.

* * * * *